United States Patent [19]

Paltauf et al.

[11] Patent Number: 5,707,978
[45] Date of Patent: Jan. 13, 1998

[54] HETEROARYL-SUBSTITUTED DEOXY GLYCERO-PHOSPHOETHANOLAMINES

[75] Inventors: Friedrich Paltauf; Albin Hermetter, both of Graz; Rudolf Franzmair, Linz, all of Austria

[73] Assignee: Clarion Pharmaceuticals Inc., Madison, Wis.

[21] Appl. No.: 485,427

[22] Filed: Jun. 7, 1995

Related U.S. Application Data

[63] Continuation-in-part of Ser. No. 344,282, Nov. 22, 1994, abandoned.

[51] Int. Cl.[6] ............... C07D 233/58; C07D 249/08; A61K 31/41; A61K 31/415
[52] U.S. Cl. ............... 514/93; 514/80; 514/91; 514/92; 514/94; 424/400; 424/450; 548/112; 548/113; 548/413; 548/414
[58] Field of Search .................. 548/112, 113, 548/413, 414; 514/80, 91, 92, 93, 94; 424/400, 450

[56] References Cited

U.S. PATENT DOCUMENTS

| | | |
|---|---|---|
| 4,372,949 | 2/1983 | Kodama et al. ............. 424/199 |
| 4,650,791 | 3/1987 | Nomura et al. ............. 514/82 |
| 5,116,992 | 5/1992 | Braquet et al. ............. 514/77 |

*Primary Examiner*—Joseph K. McKane
*Attorney, Agent, or Firm*—DeWitt Ross & Stevens S.C.

[57] ABSTRACT

Therapeutically active, heteroaryl-substituted deoxy glycero-phosphoethanolamines are disclosed having the general Formula I:

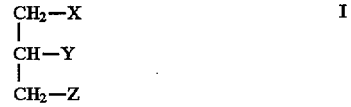

wherein one of X, Y or Z is a fatty ether substituent, one is a heteroaryl ring substituent with 1–4 nitrogens as the only heteroatoms, one of which is bonded to a carbon of the glyceryl backbone, and one is a phosphoethanolamine substituent substituted at the nitrogen, provided that each of X, Y and Z is a different substituent, and the pharmaceutical compositions comprising the therapeutically active compounds and methods of using the therapetically active compounds to treat cancerous tumors, psoriasis and inflammation are also disclosed.

31 Claims, 14 Drawing Sheets

HETEROARYL-SUBSTITUTED DEOXY GLYCERO-PHOSPHOETHANOLAMINES

This application is a CIP of Ser. No. 08/344,282 filed Nov. 22, 1994, now abandoned.

TECHNICAL FIELD

The present invention relates to novel, therapeutically active deoxy glycero-phosphoethanolamines substituted with a heteroaromatic cyclic moiety on the glyceryl backbone, pharmaceutical compositions comprising these compounds, intermediates for making the compounds, and methods of making and using the compounds. The novel, therapeutically active compounds of the invention possess anti-tumor, anti-psoriatic, and anti-inflammatory activities.

BACKGROUND OF THE INVENTION

Synthetic fatty alkyl and alkenyl ether glycerophospholipids with potential anti-tumor properties are reported in the literature. See, for example, F. Paltauf and A. Hermetter, Methods in Enzymology 197, 134–149 (1991). The compound 1-O-octadecyl-2-O-methyl-sn-glycero-3-phosphocholine (ET 18-OCH$_3$) has markedly potent anti-tumor activity. See R. Andreesen, "Ether Lipids in the Therapy of Cancer," Prog. Biochem. Pharmacol. 22, 118–131 (Karger, Basel 1988). Treatment of cancer with a fatty alkyl ether glycero-phosphoethanolamine component is also disclosed in U.S. Pat. No. 4,372,949. Halo substituted cytostatic analogs are described by H. Brachwitz et al., Chemistry and Physics of Lipids 31, 33–52 (1982). Glycerophospholipids bearing a C$_{10-24}$ alkyl ether substituent in the 1-position, a cyclic amido group in the 2-position, and a cyclic ammonio group as part of the phosphoethanolamino function in the 3-position of the glyceryl backbone are described in U.S. Pat. No. 4,650,791. Also disclosed in U.S. Pat. No. 4,650,791 are synthetic intermediates wherein the substituents are as described in the preceding sentence herein except that there is an hydroxyl group at the 3-position or hydroxyl groups at both the 1-position and the 3-position of the glyceryl backbone. Glycerophosphoethanolamines bearing a non-cyclic, substituted amino substituent in the 2-position and a lower C$_{1-5}$ alkyl ether substituent in the 1-position of the glyceryl backbone are disclosed in U.S. Pat. No. 5,116,992. Applicants are unaware, however, of the hereinafter described fatty alkyl and alkenyl ether glycero-phosphoethanolamines bearing a heteroaryl substituent.

BRIEF DESCRIPTION OF THE DRAWINGS

FIGS. 4A, 4B, and 4C present data for the compound designated CPR 1006. FIGS. 5A, 5B, and 5C present data for the compound designated CPR 1007. FIGS. 6A, 6B, and 6C present data for the compound designated CPR 1008.

DESCRIPTION OF THE INVENTION

Figure 1:
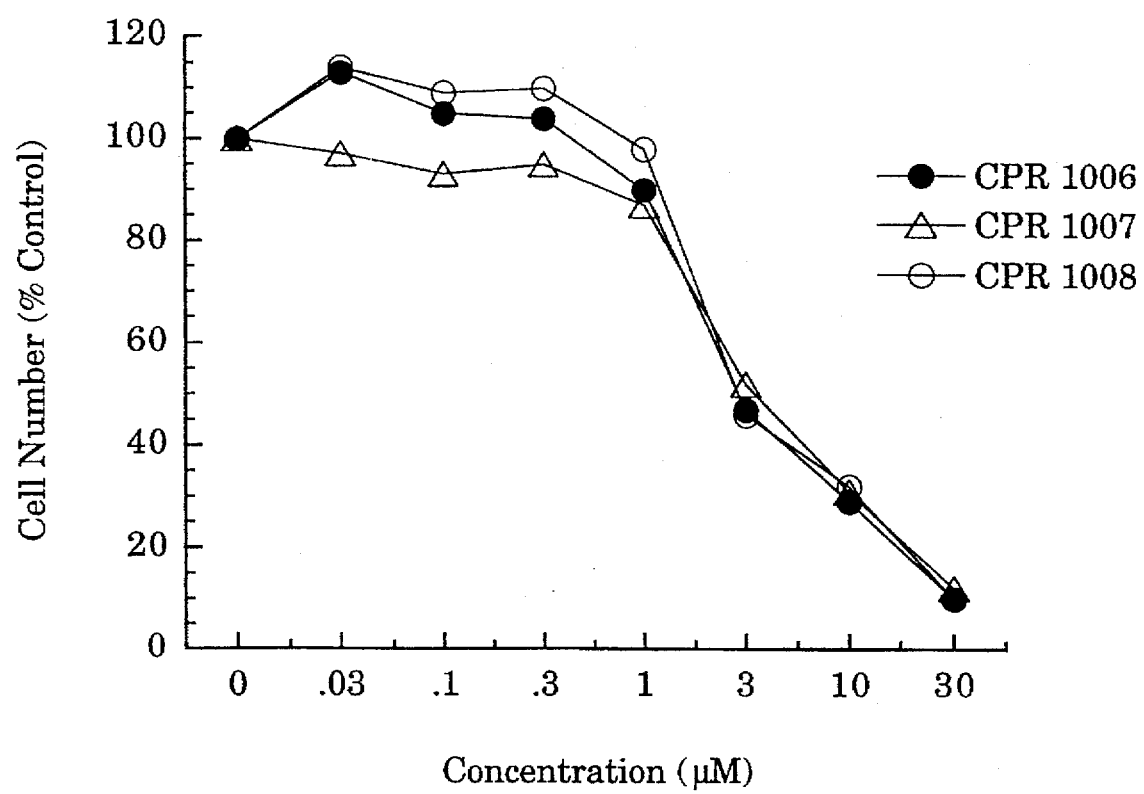
FIG. 1 is a graphical representation of results from an in vitro MCF-7 cell inhibition assay of three compounds of the invention, designated CPR 1006, CPR 1007, and CPR 1008.

The invention relates to novel, therapeutically active deoxy glycero-phosphoethanolamines, pharmaceutical compositions comprising these therapeutically active compounds, and novel intermediates for use in making the therapeutically active compounds.

The therapeutically active compounds of the invention are represented by the general formula I:

wherein one of X, Y or Z is the fatty ether substituent —O—R, one is the heteroaryl ring substituent —Het, and one is the phosphoethanolamine substituent —O—PEA, provided that X, Y and Z are each a different substituent. The symbols R, Het and PEA are defined hereinafter. The invention encompasses all of the optically isomeric and stereoisomeric forms of the compounds of general formula I as well as salts of those compounds and all of the optically isomeric and stereoisomeric forms thereof.

More particularly, the therapeutically active, heteroaryl-substituted deoxy glycero-phosphoethanolamines of the invention are represented by the general formulas Ia, Ib and Ic (collectively "the Formula I compounds"):

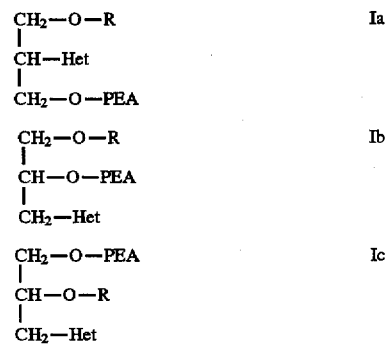

wherein the oxygens shown in FIGS. Ia, Ib and Ic are oxygens of the glyceryl backbone; R represents a substituted or unsubstituted straight or branched chain C$_{10-24}$ alkyl or alkenyl, said substituent being one or more of halo, C$_{1-3}$ alkoxy or cyano, provided that a double bond of said alkenyl does not involve the carbon atom of said alkenyl that is bonded to the oxygen of the glyceryl backbone; Het represents a 5- to 9-membered heteroaryl mono- or bicyclic ring system with 1 to 4 nitrogens as the sole heteroatoms, one of which nitrogens is bonded to the carbon of the glyceryl backbone; and PEA, together with the oxygen of the glyceryl backbone to which PEA is bonded, represents a phosphoethanolamine of the formula:

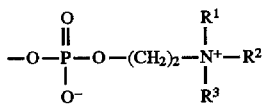

wherein $R^1$, $R^2$ and $R^3$ are each hydrogen or methyl, provided that at least one of $R^1$, $R^2$ and $R^3$ is methyl; the enantiomeric and the cis- and trans-geometric isomers thereof; and the salts thereof.

When all three of $R^1$, $R^2$ and $R^3$ are methyl, the —O-PEA moiety is known as a phosphocholine moiety. When two of $R^1$, $R^2$ and $R^3$ are methyl, the —O-PEA moiety is known as a phospho-(N,N-dimethyl)ethanolamine moiety. When only one of $R^1$, $R^2$ and $R^3$ is methyl, the —O-PEA moiety is known as a phospho-(N-methyl)ethanolamine moiety. When none of $R^1$, $R^2$ and $R^3$ is methyl, the —O-PEA moiety is known as a phosphoethanolamine moiety.

Another aspect of the present invention are novel heteroaryl substituted glycerols, which are intermediates in processes for making the Formula I compounds. These novel intermediates of the invention are represented by a modification of general formula I in which the phosphoethanolamine substituent is replaced with an hydroxyl group.

More particularly, the intermediates of the invention are represented by the general formulas IIa, IIb and IIc (collectively "the Formula II compounds"):

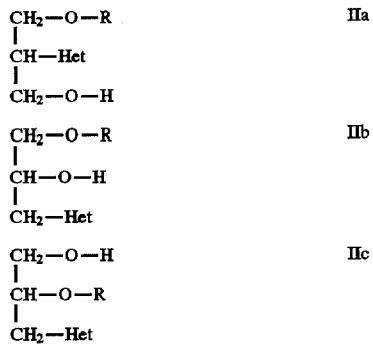

wherein the oxygens shown in FIGS. IIa, IIb and IIc are oxygens of the glyceryl backbone; wherein R and Het are as defined above for the Formula I compounds; the enantiomeric and the cis- and trans-geometric isomers thereof; and the salts thereof.

As used herein, R is selected from the group consisting of (1) substituted or unsubstituted, preferably unsubstituted, $C_{10-24}$ alkyl groups, preferably $C_{14-20}$ alkyl and especially preferred $C_{16-18}$ alkyl, such as, for example, tetra-, penta-, hexa- hepta-, octa-, nonadecyl-, eicosyl-, or the branched analogs thereof; and (2) substituted or unsubstituted, preferably unsubstituted, $C_{10-24}$ alkenyl groups, preferably $C_{14-20}$ alkenyl and especially preferred $C_{16-18}$ alkenyl, whereby a double bond of the alkenyl group does not involve the carbon atom of said alkenyl that is bonded to the oxygen of the glkyceryl backbone. Both the aforementioned alkyl and alkenyl groups can be substituted at one or more carbons, preferably at one, with substituents which do not interfere with syntheses of the compounds during the synthetic steps of making them. Preferred substituents are halo, $C_{1-3}$ alkoxy or cyano. The term "halo" refers to any of the four halogens, chloro, bromo, iodo and fluoro, with chloro and fluoro being preferred.

Typical of the heteroaryl ring moieties included within the term "Het" are such 5- to 9 membered rings, including single and fused ring entities such as, for example, pyrrolyl, pyrazolyl, imidazolyl, 1,2,3-triazolyl, 1,2,4-triazolyl (also denoted as 1-triazolyl), tetrazol-1-yl, indolyl, benzimidazolyl, benztriazolyl, purinyl and the like, with imidazolyl and 1,2,4-triazolyl being preferred. Said rings may also be substituted with one or more substituents, preferably one, such as $C_{1-3}$ alkyl, $C_{1-3}$ alkoxy or a polar substituent such as cyano, nitro or methylsulfono. Typical of such substituted heteroaryl ring moieties are, for example, 1-(2-methylimidazolyl), 1-(4-methoxyindolyl), 1-(4-cyanobenztriazolyl) and the like. As used hereinafter, the term "Het-Compound" represents the heteroaryl ring moiety with its additional hydrogen, i.e., Het—H, for example, pyrrole, pyrazole, imidazole, triazole and the like.

The preferred Formula I compounds, and the most preferred, which are of Formula Ia, are those wherein R is $C_{16-18}$ alkyl, Het is imidazolyl or 1,2,4-triazolyl, and —O-PEA is phosphocholine, for example:

1-O-octadecyl-2-(1-imidazolyl)-2-deoxy-glycero-3-phosphocholine (which is designated "CPR 1006");

1-O-octadecyl-2-(1-triazolyl)-2-deoxy-glycero-3-phosphocholine (which is designated "CPR 1007"); and 1-O-hexadecyl-2-(1-imidazolyl)-2-deoxy-glycero-3-phosphocholine (which is designated "CPR 1008").

Other particular compounds of Formula Ia are:

1-O-octadecyl-2-(1-imidazolyl)-2-deoxy-glycero-3-phospho-(N-methyl) ethanolamine;

1-O-hexadecyl-2-(1-(4-methoxyindolyl))-2-deoxy-glycero-3-phosphocholine;

1-O-tetraeicosyl-2-(1-tetrazolyl)-2-deoxy-glycero-3-phospho-(N,N-dimethyl) ethanolamine;

1-O-hexadecyl-2-(1-(4-cyanobenztriazolyl))-2-deoxy-glycero-3-phosphocholine;

1-O-(trans-9-octadecenyl)-2-(1-imidazolyl)-2-deoxy-glycero-3-phospho-(N-methyl)ethanolamine; and S-1-O-tetradecyl-2-purinyl-2-deoxy-glycero-3-phosphocholine.

Particular compounds of Formula Ib are:

R-1-O-hexadecyl-3-(1-imidazolyl)-3-deoxy-glycero-2-phosphocholine;

1-O-octadecyl-3-indolyl-3-deoxy-glycero-2-phospho-(N,N-dimethyl)ethanolamine;

1-O-(cis-9-hexadecenyl)-3-(1-tetrazolyl)-3-deoxy-glycero-2-phosphocholine; and

1-O-hexadecyl-3-(2-methylimidazolyl)-3-deoxy-glycero-2-phosphocholine.

Particular compounds of Formula Ic are:

1-(1-imidazolyl)-1-deoxy-2-O-hexadecyl-glycero-3-phosphocholine;

1-(1-triazolyl)-1-deoxy-2-O-(2-chloro-octadecyl)-glycero-3-phospho-(N-methyl)ethanolamine;

1-pyrrolyl-1-deoxy-2-O-(2-methoxy-octadecyl)-glycero-3-phosphocholine; and 1-(1-tetrazolyl)-1-deoxy-2-O-(9-octadecenyl)-glycero-3-phosphocholine.

The invention also comprehends salts of the compounds of the invention, including both the Formula I compounds and the Formula II compounds described hereinabove. These salts include acid addition salts, such as, for example, those made with hydrochloric, hydrobromic, nitric, sulfuric, phosphoric, carbonic, acetic, citric or lactic acids. The salts may also include those made with bases, such as, for example, sodium hydroxide, potassium hydroxide or calcium hydroxide. The salts of the invention are made by conventional methods well known to the skilled. The salts for therapeutic use of the Formula I compounds are pharmaceutically acceptable salts, as understood in the art.

CHEMISTRY

The compounds of the present invention may be prepared by the stepwise procedures outlined in the following Reaction Schemes and subsequent examples. As used in the Reaction Schemes, the symbols R, $R^1$, $R^2$, $R^3$, PEA, and Het are as previously defined, the symbol Tr represents trityl, i.e., triphenylmethyl, and the symbol Ph represents phenyl. The thus-obtained compounds in the Reaction Schemes may be purified by conventional methods of the art, e.g. chromatography, recrystallization, etc.

The Formula I compounds and Formula II compounds have an asymmetric carbon atom (C2 position in the glyceryl backbone) in their structures. Consequently these compounds may exist in the form of different R and S optically isomeric forms (enantiomers) or racemates. Substantially pure forms of either of the R- and S-isomer may be obtained, substantially free of the other, by the application of art-known resolution methodologies such as, for example, column chromatography using chiral columns, starting preparation from the R- or S-isomer of an appropriate precursor, for example, the starting Compound (A) shown in Reaction Scheme I hereinbelow.

In addition, cis- and trans-geometric isomers may also be present in the subject compounds, e.g. when R in Formulas I or II is $C_{10-24}$ alkenyl, due to the cis- and trans-configuration inherent with the double bond. Thus, by initially starting with an appropriate cis- or trans-precursor, the corresponding end product of the Formulas I compound or Formula II compound will be obtained.

All isomeric forms of the Formula I compounds and Formula II compounds, including pure enantiomeric and geometric isomers and mixtures thereof, are intended to be within the scope of this invention. Unless otherwise specified, the compounds of the hereinafter examples are in racemic form.

Working up the individual stepwise products indicated in the following Reaction Schemes is advantageously carried out by standard methodologies, for example, by evaporating solvent from the reaction solution or precipitating the product from the reaction solution by dilution of the solution with an appropriate antisolvent (a solvent in which the product is less soluble than in the solvent of the reaction solution). The crude intermediate products obtained may be quite suitable, without further purification operations, for the preparation of the final products, which then may be purified. Particularly suitable methods for purifying the Formula I and Formula II compounds are the conventional chromatographic methods, such as preparative thin-layer chromatography (TLC), column chromatography, adsorption chromatography, medium pressure liquid chromatography (MPLC) or high pressure liquid chromatography (HPLC).

REACTION SCHEME 1

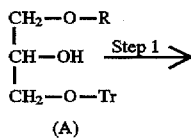
(A)

—continued
REACTION SCHEME 1

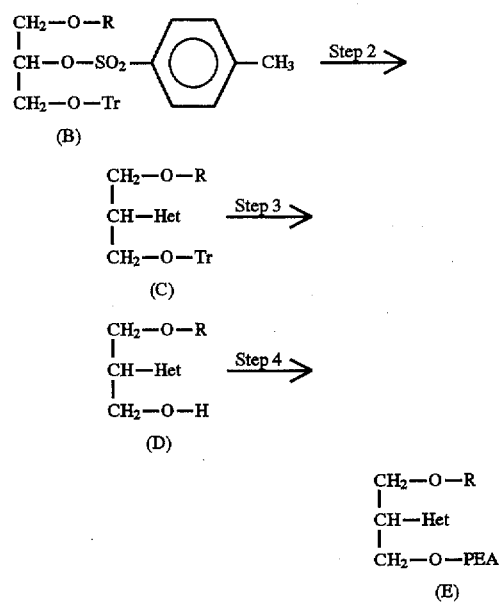

Step 1

The compounds of Formula (A) are known in the literature or are obtainable by art-recognized procedures. See, for example, A. Hermetter and F. Paltauf, Procedures for the Synthesis of Ether Lipids, p. 393 et. seq., in H. K. Mangold and F. Paltauf, "Ether Lipids", Academic Press, 1983, and F. Paltauf and A. Hermetter, Methods Enzymol. 197, 134–149 (1991). A solution of compound (A) in an amphoteric aprotic solvent, e.g. pyridine, tetrahydrofuran, dioxane or the like, is added dropwise with stirring to a solution of a stoichiometric amount of p-toluenesulfonyl chloride, preferably in solution with the same solvent. The reaction mixture may be maintained at room temperature until the reaction is essentially completed, and then subjected to conventional workup, for example, with appropriate organic extraction solvents, aqueous washes, drying, solvent evaporation, recrystallization and the like procedures, to yield the desired 2-p-toluenesulfonyl derivative (B).

Step 2

Compound (B) is reacted with a stoichiometric amount of the desired Her-Compound in anhydrous dimethyl sulfoxide in the presence of sodium dimethylsulfinylmethide. Elevated temperatures are advantageously employed to enhance the rate of reaction, e.g. about 100° C. After the reaction is completed, conventional workup yields the desired 2-Het derivative (c).

Step 3

Removal of the trityl function in Compound (C) to yield Compound (D) is readily accomplished by art-recognized procedures, e.g. by reaction with boron trifluoride in an appropriate organic solvent, e.g., methanol, at low to ambient temperature (see A. Hermetter and F. Paltauf, Chem. Phys. Lipids 29, 191 (1981)), followed by conventional workup.

Step 4

The phosphoethanolamine moiety (PEA) is introduced by reaction of the hydroxyl in Compound (D) with 2-chloro-2-oxo-1,3,2-dioxaphospholane in an inert organic aprotic solvent, such as, for example, toluene (preferred), benzene, chloroform, diethyl ether, dioxane and the like, followed by reaction with an appropriate amine,

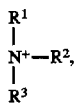

to yield the desired compound (E).

REACTION SCHEME 2

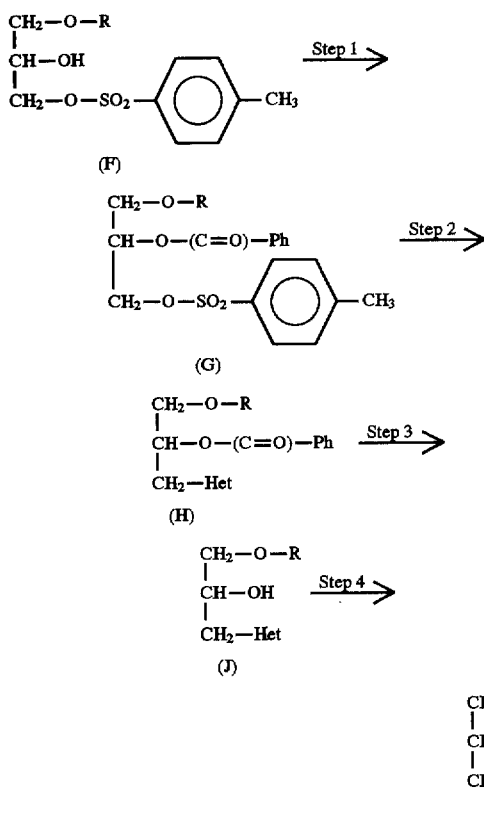

Step 1

The compounds of Formula (F) are known or are obtainable by art recognized procedures, for example, see P. N. Guivisdalsky and R. Bittman, J. Org. Chem. 54, 4637–4642 (1989). In general, as illustrated below, the epoxide of glycidyl tosylate is opened in the presence of boron trifluoride catalyst for reaction with the aliphatic alcohol, ROH, in an aprotic solvent, e.g., chloroform, to yield (F):

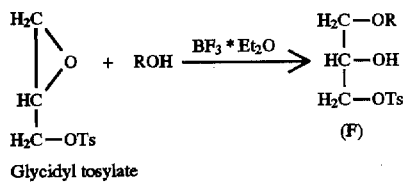

The R-, S- and racemic forms of glycidyl tosylate are commercially available and, accordingly, can be used as starting materials for making the enantiomers or racemates of compounds of Formula (F).

Step 1 is carried out to avoid side reactions in Step 2. Thus, the hydroxyl function of the compound of Formula (F) is protected under mild conditions by, for example, conventional acylation with a stoichiometric excess of benzoic acid chloride (Ph—(C=O)Cl) in an appropriate aprotic solvent, for example, toluene, chloroform, methylene chloride or the like and an excess of a sterically hindered base, for example, diisopropyl-ethylamine, at a temperature ranging from room temperature to the boiling point of the chosen solvent. After completion of the reaction, conventional workup yields the desired compound of Formula (G).

Step 2

Compound (G) is reacted with a stoichiometric amount of the desired Het-Compound in anhydrous dimethyl sulfoxide in the presence of sodium dimethylsulfinylmethide. Elevated temperatures, e.g., about 100° C., are advantageously employed to enhance the rate of reaction. After the reaction is completed, conventional workup yields the desired 1-Het derivative of Formula (H).

Step 3

Removal of the protecting benzoyl group is readily accomplished by saponification with an excess of a strong inorganic base such as sodium or potassium hydroxide in aqueous solution. The aqueous base is added to a solution of the compound of Formula (H) in an appropriate amphoteric, protic or aprotic solvent such as, for example, methanol, ethanol, isopropanol, pyridine, dioxane or the like. After completion of the reaction, conventional workup yields the desired compound of Formula (J)

Step 4

The phosphoethanolamine moiety is introduced by reaction of the hydroxyl in Compound (J) with 2-chloro-2-oxo-1,3,2-dioxaphospholane in an inert organic aprotic solvent, such as, for example, toluene (preferred), benzene, chloroform, diethyl ether, dioxane and the like, followed by reaction with an appropriate amine,

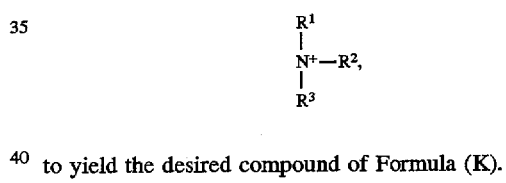

to yield the desired compound of Formula (K).

REACTION SCHEME 3

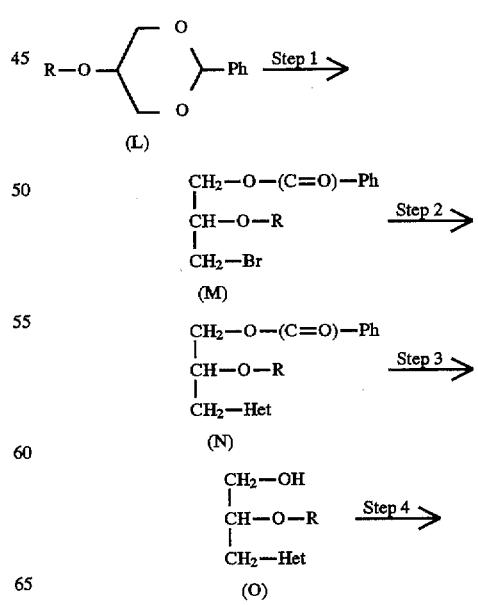

-continued
REACTION SCHEME 3

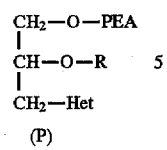

(P)

Step 1

The compounds of Formula (L) are readily obtained from the known precursor, 1,3-benzylidene-glycerol, with introduction of the R moiety analogous to the synthesis of 1-O-hexadecyl-2,3-isopropylidene-glycerol described by A. Hermetter and F. Paltauf, Procedures for the Synthesis of Ether Lipids, p. 391 et seq., in H. K. Mangold and F. Paltauf, Ether Lipids, Academic Press, 1983. Oxidative ring opening of the Formula (L) compound is carried out by treatment with a slight excess of N-bromosuccinimide (NBS) in carbon tetrachloride in the presence of excess barium carbonate. After the reaction is complete, conventional workup yields the compound of Formula (M).

Step 2

Compound (M) is reacted with the desired Het-Compound as described in Step 2 of Reaction Scheme 1 to yield the Het-derivative of Formula (N).

Step 3

Debenzoylation of the protected hydroxyl function of Compound (N) is carried out as described for Compound (H) in Reaction Scheme 2 to yield the Formula (O) compound.

Step 4

Compound (O) is converted to Compound (P) under the same reaction conditions and molar ratios as described in Step 4 of Reaction Scheme 1.

REACTION SCHEME 4
This reaction scheme provides an alternative chemical synthetic route for making the formula (P) Compounds:

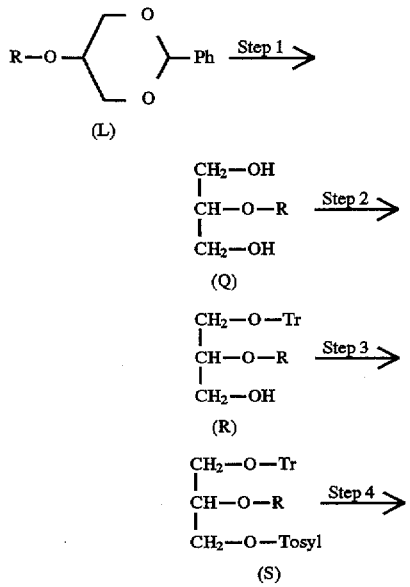

-continued
REACTION SCHEME 4
This reaction scheme provides an alternative chemical synthetic route for making the formula (P) Compounds:

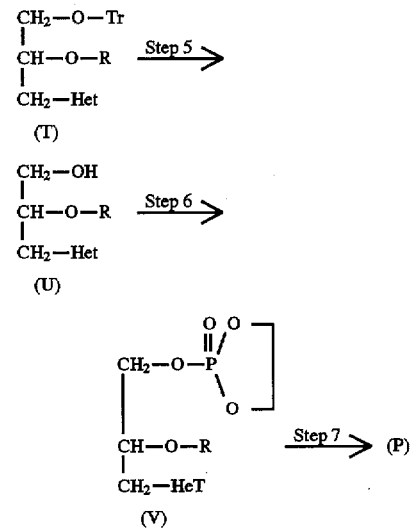

Step 1

The compounds of Formula (Q) are either known or readily obtainable from 2-OR-1,3-benzylideneglycerol (see Compounds of Formula (L) in Reaction Scheme 3) by conventional acid-catalyzed hydrolysis, for example, hydrochloric acid in methanol, of the benzylidene protective group, following procedures described in the literature; see, for example, E. O. Oswald et al., Lipids 1, p. 121 (1966); and A. Hermetter and F. Paltauf, Procedures for the Synthesis of Ether Lipids, pp. 391–392, in H. K. Mangold and F. Pailauf, Ether Lipids, Academic Press, 1983).

Step 2

Compound (Q) is tritylated in the conventional manner, for example, by reaction with triphenylchloromethane in an aprotic solvent, for example, pyridine, under anhydrous conditions at room temperature. After completion of the reaction, conventional workup yields the desired trityl derivative (R).

Step 3

A solution of Compound (R) in an amphoteric aprotic solvent, e.g., pyridine, tetrahydrofuran, dioxane or the like, is added dropwise with stirring to a solution of p-toluenesulfonyl chloride, preferably in solution with the same solvent. The reaction mixture may be maintained at room temperature until the reaction is essentially completed, and then subjected to conventional workup to yield the desired tosyl derivative (S).

Step 4

Replacement of the —O-Tosyl function in Compound (S) with a Het function is readily accomplished by the reaction of Compound (S) with the desired Het-Compound in anhydrous dimethyl sulfoxide in the presence of sodium dimethylsulfinyl methide, followed by conventional workup to yield the desired 1-Het derivative of Formula (T).

Step 5

Removal of the trityl function in Compound (T) to yield Compound (U) is readily accomplished by art-recognized procedures, similar to Step 3 in Reaction Scheme 1.

Steps 6 and 7

The phosphoethanolamine moiety (PEA) is introduced by reaction of the hydroxyl in compound (U) with 2-chloro-2-oxo-1,3,2-dioxaphospholane in an inert organic aprotic solvent to yield Compound (V), followed by reaction with an appropriate amine, $NR^1R^2R^3$, to yield the desired Compound (P), similar to Step 4 in Reaction Scheme 1.

UTILITY

The Formula I compounds, including the isomeric forms thereof and the pharmaceutically acceptable salts of those compounds (including all of the isomeric forms), are useful chemopreventive and adjuvant agents for the treatment of cancerous tumors and are useful therapeutic agents for treating inflammation and hyperproliferative skin diseases such as psoriasis.

A. ANTI-TUMOR

The anti-tumor activity of both naturally occurring and synthetic glycerol-derived ether lipids has been confirmed in the literature. See, for example, R. Andreesen, "Ether Lipids in the Therapy of Cancer", Prog. Biochem. Pharmacol., vol.22, pp. 118–131 (Karger, Basel 1988).

The following testing procedures using human tumor cell lines in in vitro assays, including the antitumor/anti-cancer screens conducted by the (NCI), demonstrate the marked anti-tumor (or antineoplastic) activity of the therapeutically useful compounds of the invention.

Assay

Figure 2:
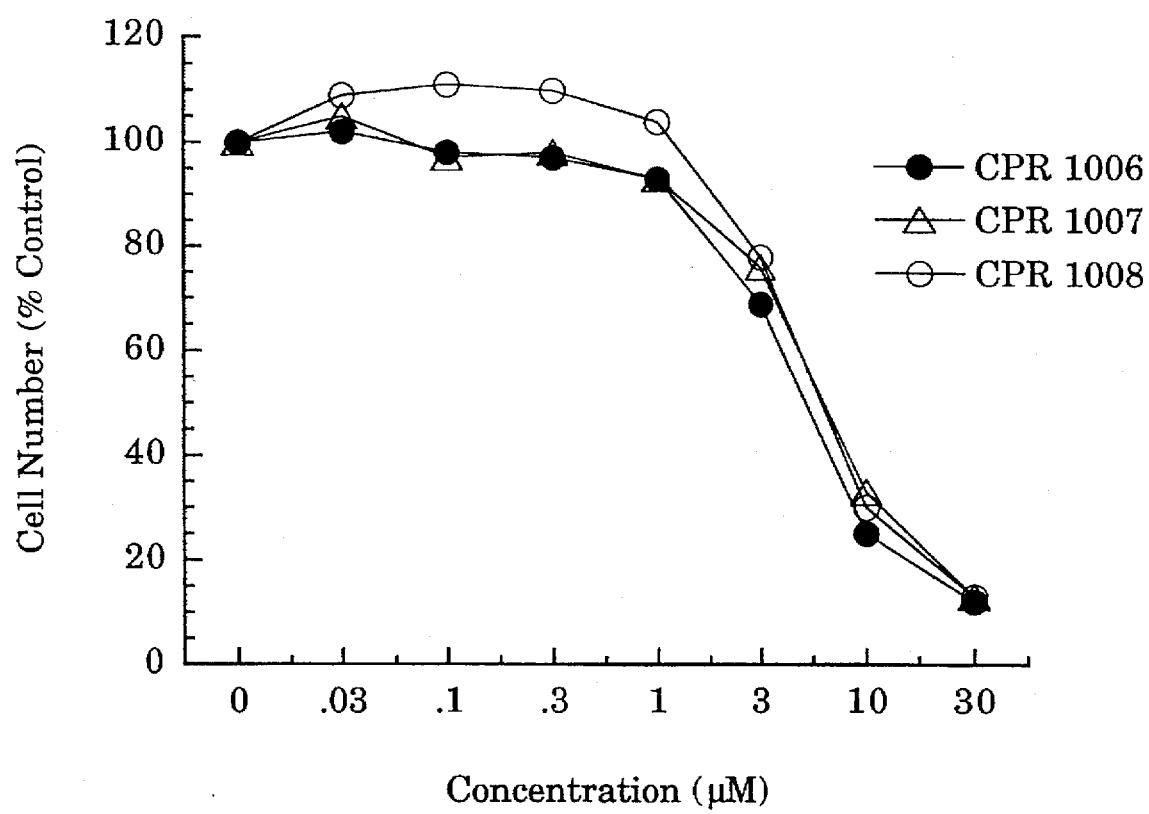
FIG. 2 is a graphical representation of results from an in vitro MDA-MB-231 cell inhibition assay of three compounds of the invention, designated CPR 1006, CPR 1007, and CPR 1008.
Figure 3:
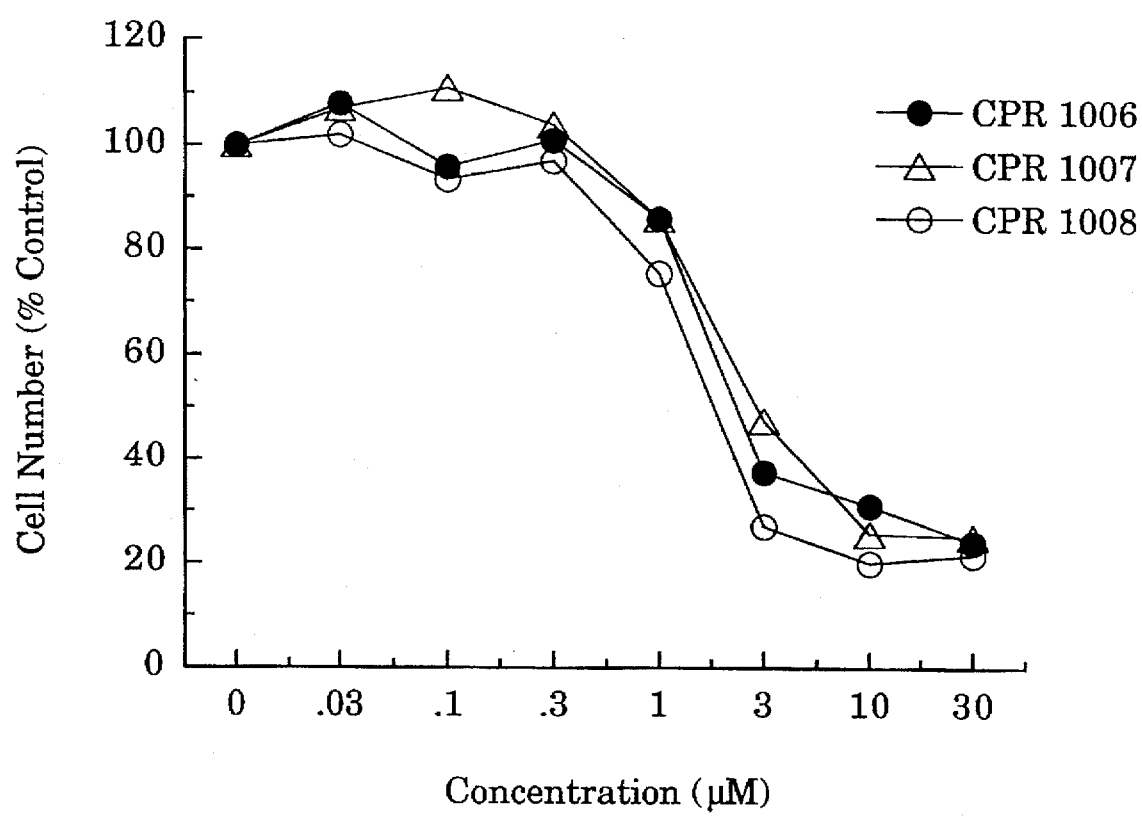
FIG. 3 is a graphical representation of results from an in vitro HL-60 cell inhibition assay of three compounds of the invention, designated CPR 1006, CPR 1007, and CPR 1008.

1. Human tumor cell lines, obtainable from the American Type Culture Collection (ATCC)
   a. MCF-7 (ATCC HTB 22): an estrogen receptor positive human breast carcinoma cell line (attachment dependent);
   b. MDA-MB-231 (ATCC HTB 26): an estrogen receptor negative human breast carcinoma cell line (attachment independent); and
   c. HL 60 (ATCC CCL 240): a promyelocytic leukemia cell line.
2. Culture media
   a. For cell lines 1-a and 1-b: Dulbecco's Modified Eagle's Medium (DMEM) plus 10% Fetal Bovine Serum (FBS); and
   b. For cell line 1-c: Roswell Park Memorial Institute-1640 (RPMI-1640) plus 20% FBS.
3. Standard protocol for culturing cell lines: in T-75 or T-150 flasks; 37° C.; 95% air, 5% $CO_2$; 100% humidity
   a. Cell lines 1-a and 1-b are passaged when approximately 80% confluent; with trypsin (1 mg/mL) and EDTA (1 mM EDTA in Ca-Mg free Hank's balanced salt solution); at a 1:4 to 1:5 split.
   b. Cell line 1-c is passaged by removing approximately 75% of the media and cell mixture and adding an equal amount of fresh media once or twice a week.
   c. All procedures are performed aseptically in a Class II biological safety cabinet using standard BL-2 containment procedures. In order to prevent genetic drift in stock cell lines, fresh cultures are prepared at approximately monthly intervals with cells thawed from liquid nitrogen storage.
4. Methodology
   a. After cell passage, count cells with a hemocytometer;
   b. Adjust concentration to approximately 10,000 cells per 100 µL;
   c. Pipette 100 µL cell suspension into each well of a standard 96-well microtiter plate;
   d. Preincubate 24 hours to allow cells to attach;
   e. Add test compound dissolved in PEG-200 to achieve final concentration levels ranging from 0 to 30 µM; and
   f. Incubate 48 hours under standard culture conditions and determine end points.
5. End Point (for cell lines 1-a and 1-b)
   a. Remove media and add approximately 100 µL/well of cold methanol (0°–5° C.);
   b. After 1 minute, remove methanol;
   c. Add approximately 100 µL crystal violet (CV) stain. (To prepare CV stain: dissolve 14 g dry crystal violet in 100 mL absolute ethanol; immediately before use, dilute 1 mL with 30 mL distilled water);
   d. After 15 minutes, remove stain and rinse cells with distilled water to remove residual stain;
   e. Air-dry plates;
   f. Read results from the wells using a standard 96-well microtiter plate reader (measuring absorbance at 600 nm);
   g. Results: single point reading: the higher the absorbance, the higher the cell number; control—no test compound present in culture medium; calculate: Cell Number (as % of Control)=A(compound)×100, where A(compound) A(control) is absorbance with test compound present in the culture medium and A(control) is absorbance of control;
   h. Calculate: $IC_{50}$=Inhibitory Concentration 50%.
   i. Results are represented in FIGS. 1 and 2, which illustrate the marked inhibition of cell growth at concentrations above 1 µM of the compounds tested.
6. End Point (for cell line 1-C)
   a. Follow assay directions provided with kit commercially available from Promega Corporation, Madison, Wis., USA under the name "CellTiter 96™ AQ$_{ueous}$ Non-Radioactive Cell Proliferation Assay" (The assay is a non-radioactive, colorimetric method for determining number of viable cells based on cellular conversion of the tetrazolium salt, MTS, into a formazan that is soluble in tissue culture medium and is measured at 490 nm directly from 96-well assay plates without additional processing. See A. H. Cory et al., Cancer Commun. 3, 207 (1991); T. L. Riss and R. A. Moravec, Mol. Biol. Cell. 3 (Suppl.), 184a (1992); T. M. Buttke et al., J. Immunol. Methods 157, 233 (1993));
   b. Read absorbance in the wells at 490 nm using a standard 96-well microtiter plate reader; the absorbance correlates with the cell number; determine Cell Number (as % of Control) following step 5 (g) above.
   c. The results are represented in FIG. 3, which illustrates the marked inhibition of cell growth at concentrations above 0.3 µM of the compounds tested.

Further evidence of the anti-tumor activity of the Formula I compounds are the results obtained in the NCI anti-cancer screening of such compounds against more than 50 different cell lines. In the mean graphs of FIGS. 6–8, the relative sensitivity of each cell line to the test compound compared with the average sensitivity to the compound of all of the lines listed (and tested) is depicted in graphic form. The mean graph is constructed by projecting bars to the right or left of the mean sensitivity of all of the cell lines, depending on whether the sensitivity of a cell line is either greater or less, respectively, than the average sensitivity of all of the lines. Furthermore, the length of each bar is proportional to the relative sensitivity (relative to the mean sensitivity of all cell lines) of the cell line corresponding to the bar. A more detailed description of the NCI screen for anti-tumor/anti-cancer activity and mean graphs to depict results from screening a composition are reported by M. R. Grever et al., "The National Cancer Institute: Cancer Drug Discovery and Development Program", Seminars in Oncology, Vol. 19, No. 6 (December), 1992: pp.622–638.

Figure 4A:
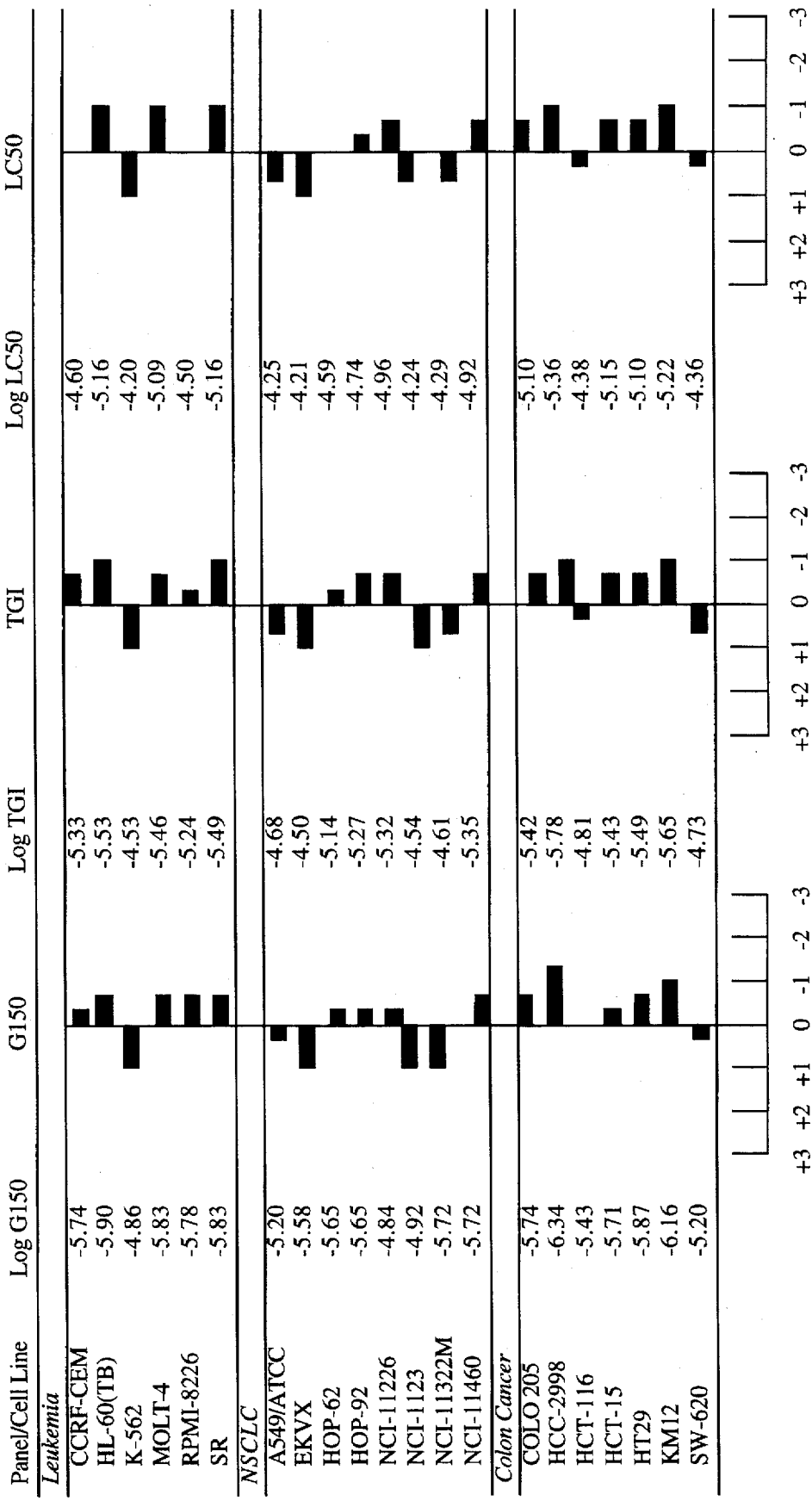
FIGS. 4A, 4B, 4C, 5A, 5B, 5C, 6A, 6B, and 6C present mean graphs from United States National Cancer Institute ("NCI") anti-cancer screening of compounds of the invention against multiple cell lines.
Figure 4B:
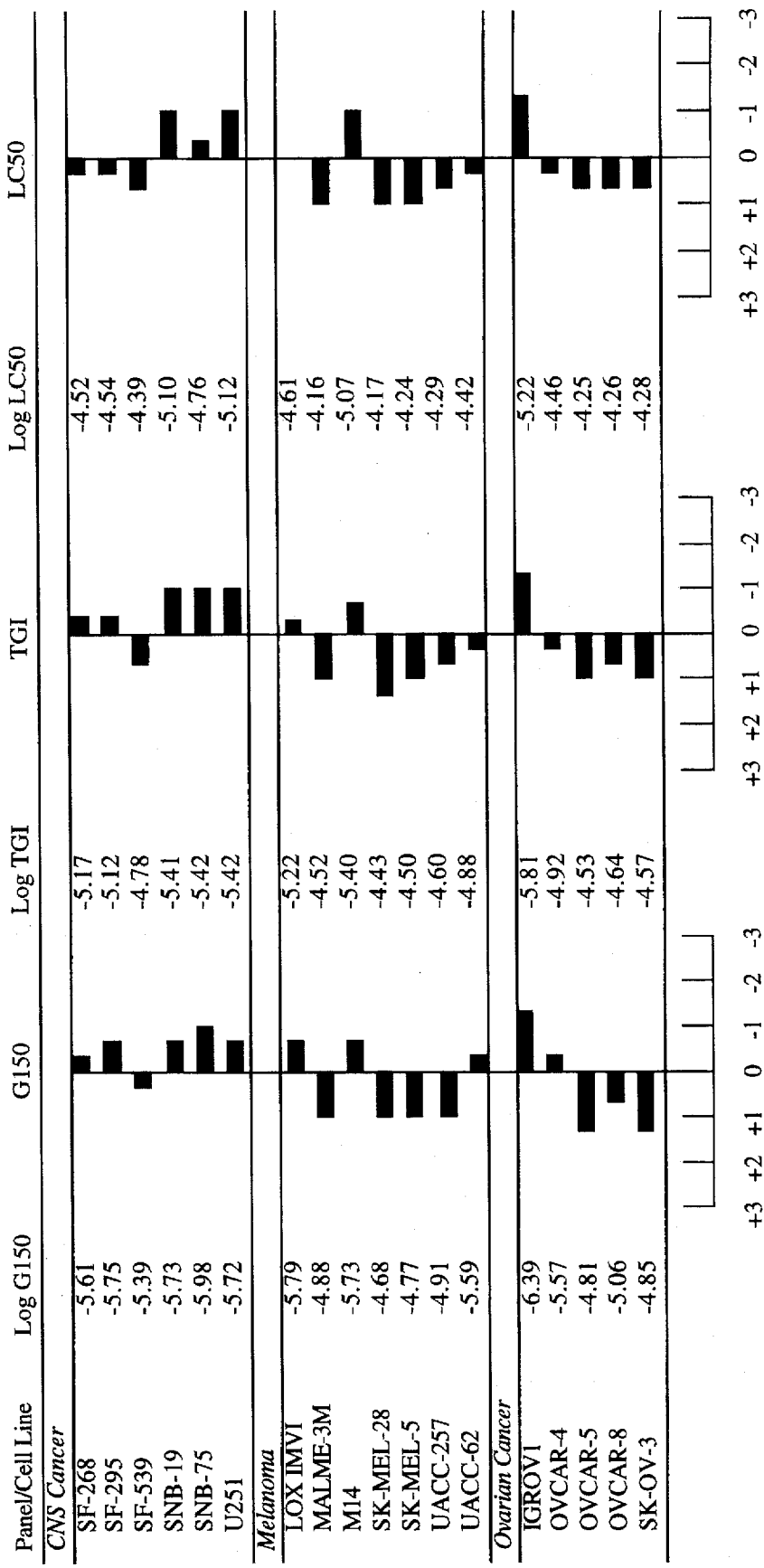
Figure 4C:
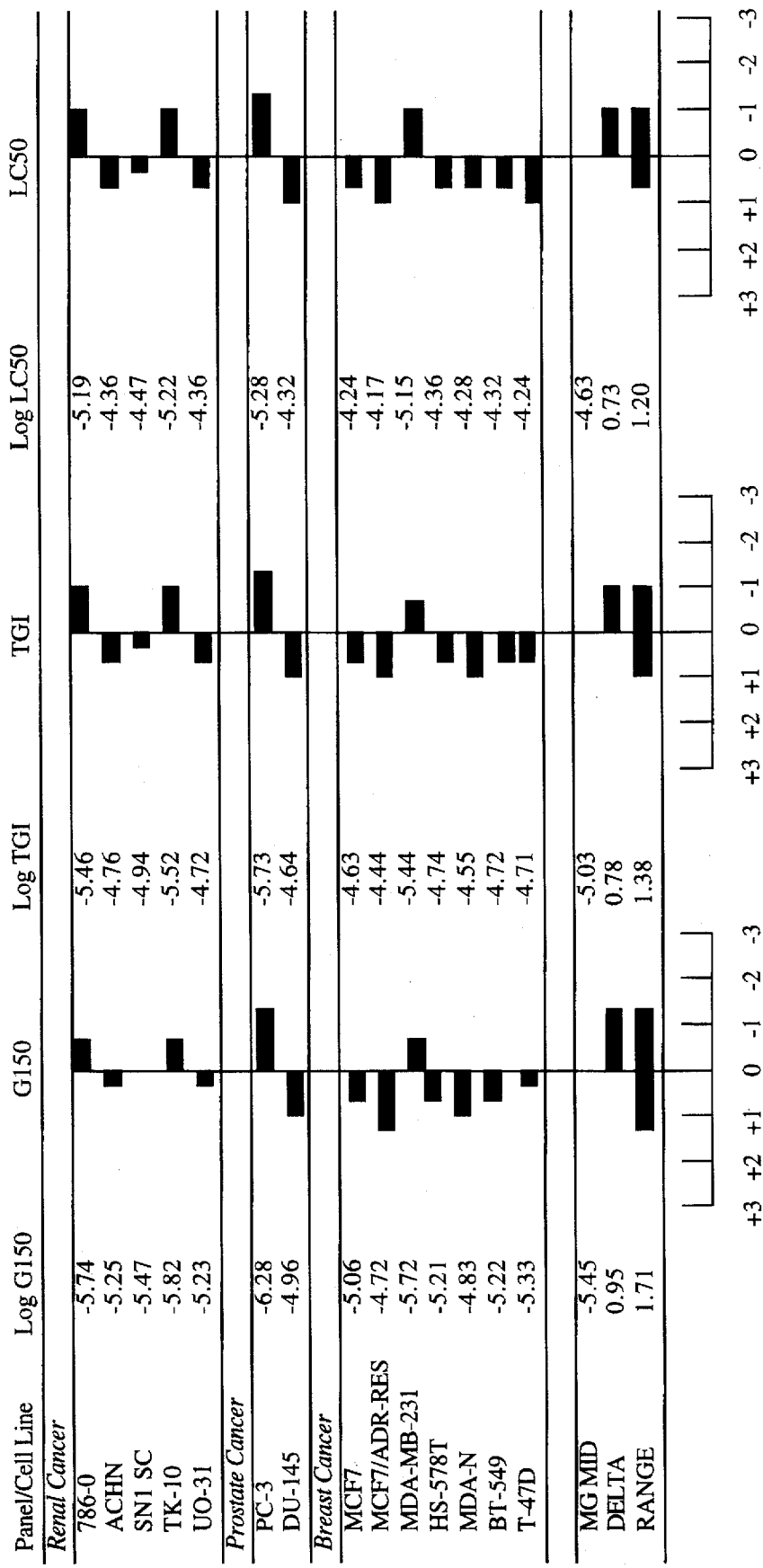

FIGS. 4A 4B, and 4C depict a mean graph from NCI anti-tumor/anti-cancer screening for the compound 1-O-octadecyl-2-(1-imidazolyl)-2-deoxy-glycero-3-phosphocholine (CPR 1006).

Figure 5A:
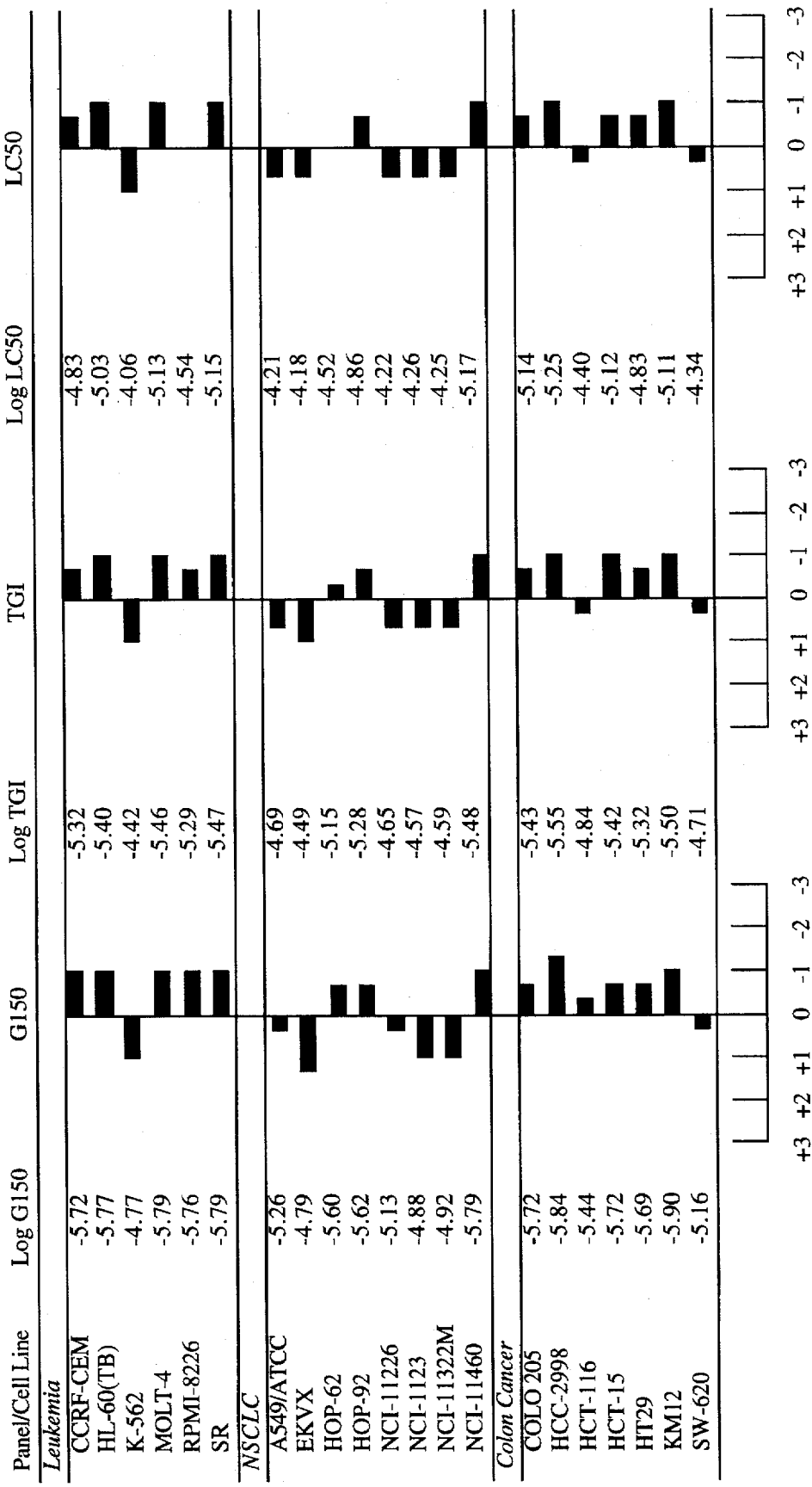
Figure 5B:
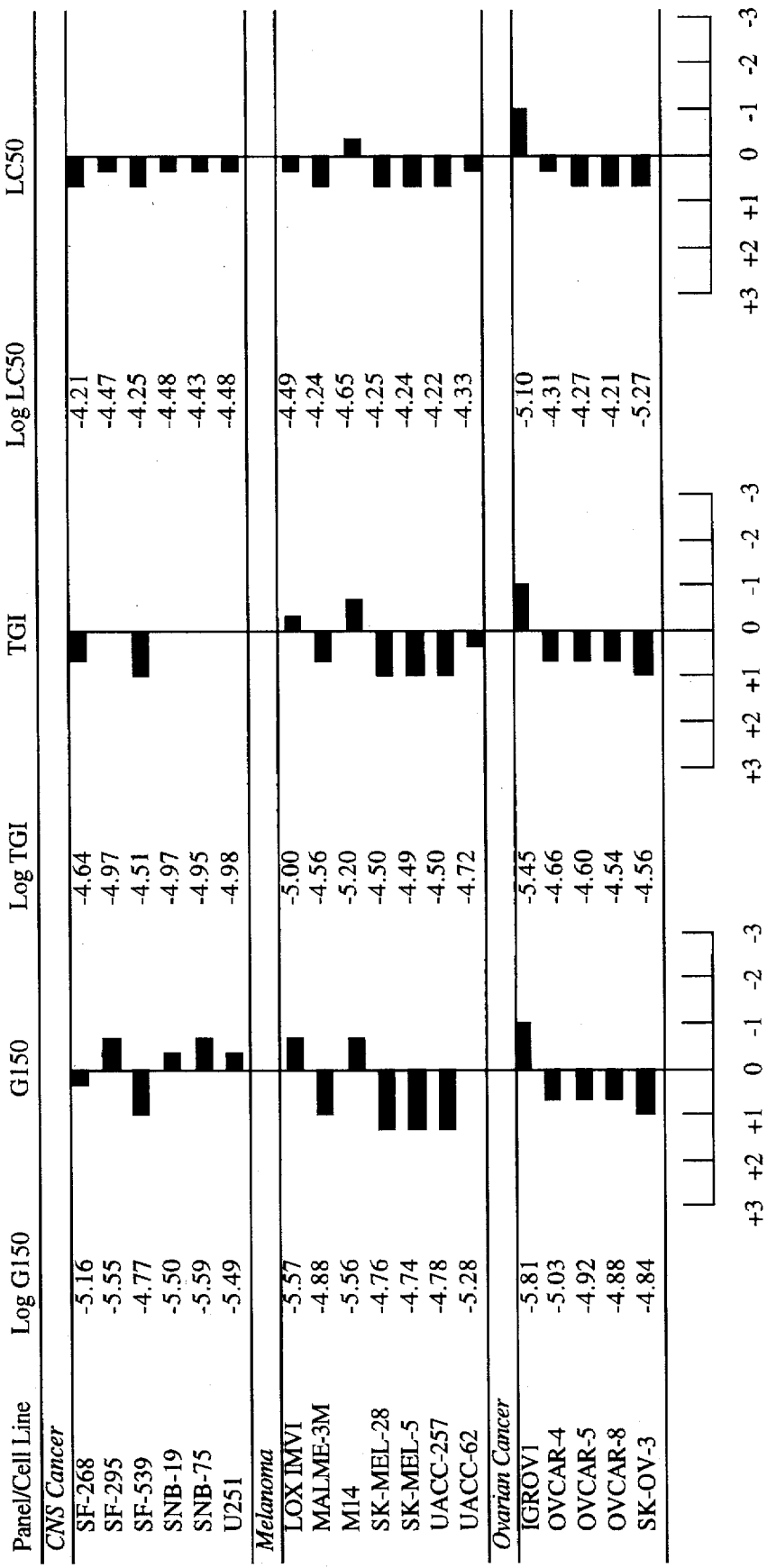
Figure 5C:
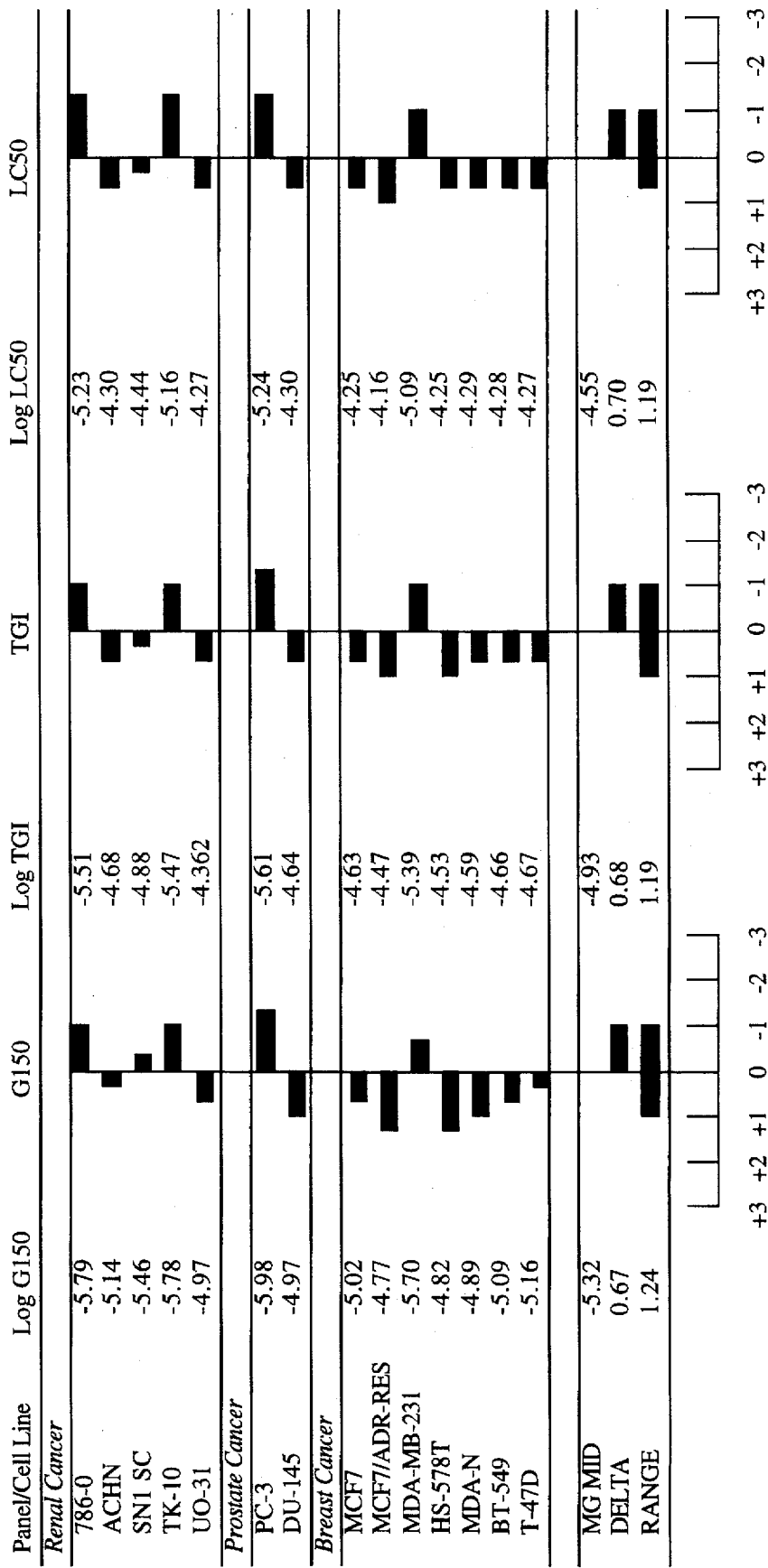

FIGS. 5A, 5B, and 5C depict a mean graph from NCI anti-tumor/anti-cancer screening for the compound 1-O-octadecyl-2-(1-triazolyl)-2-deoxy-glycero-3-phosphocholine (CPR 1007).

Figure 6A:
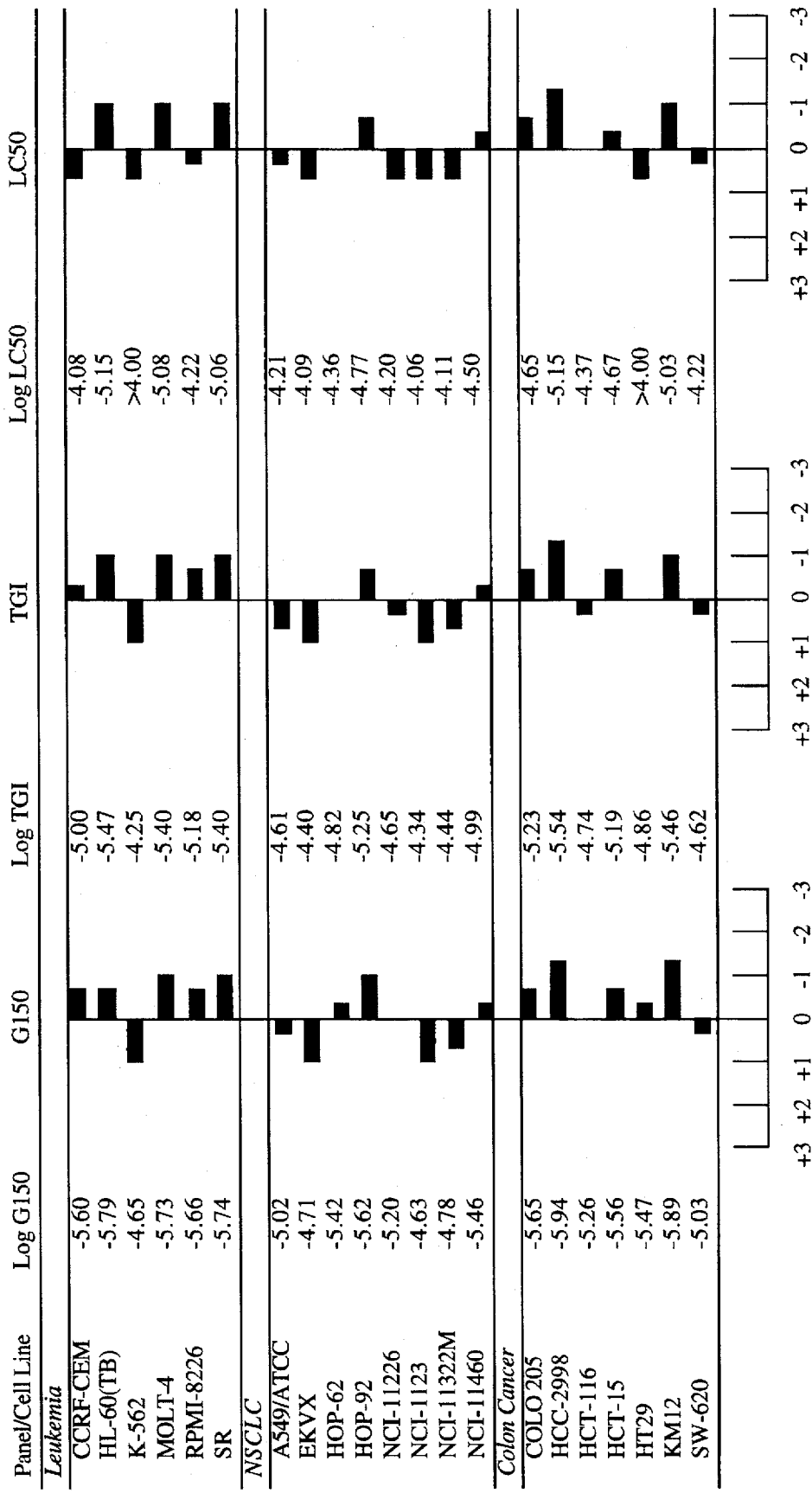
Figure 6B:
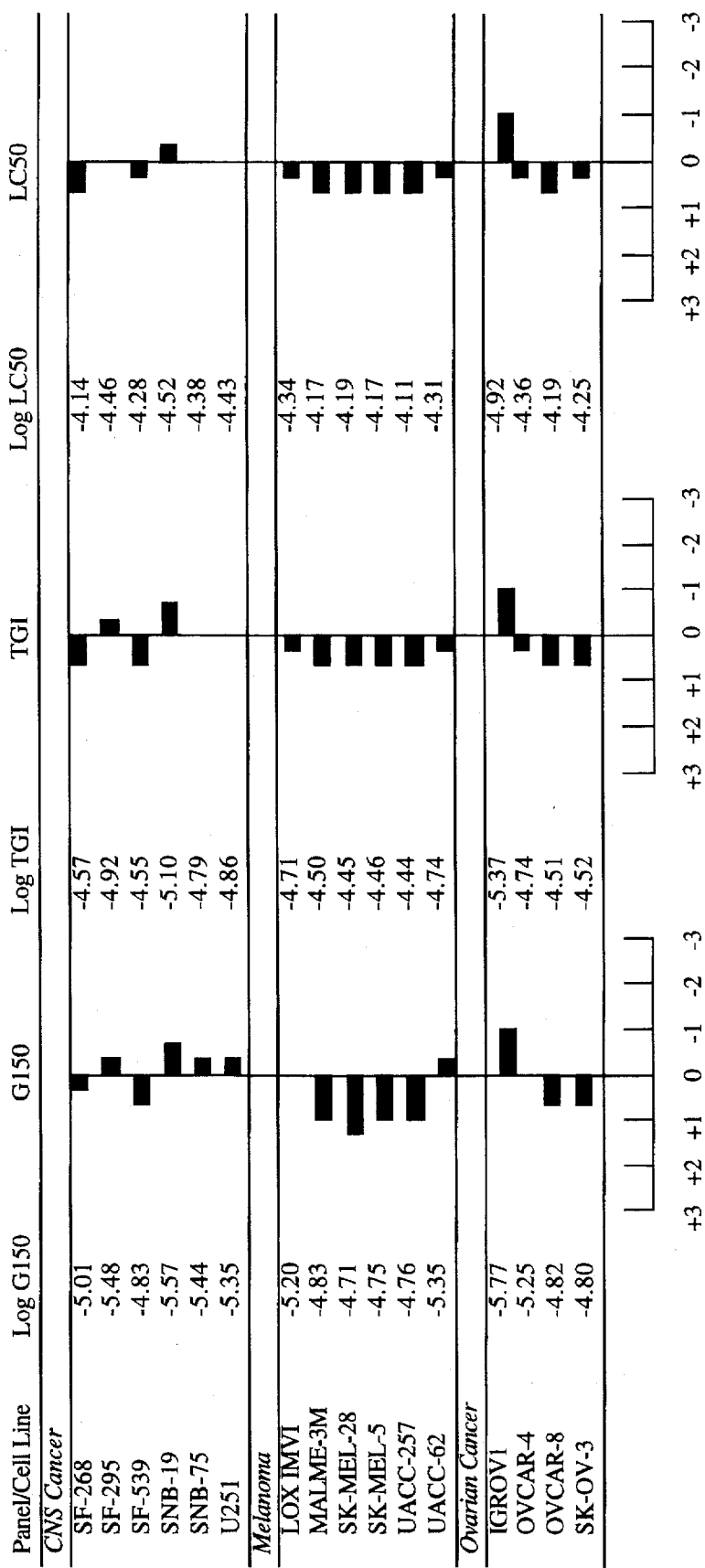
Figure 6C:
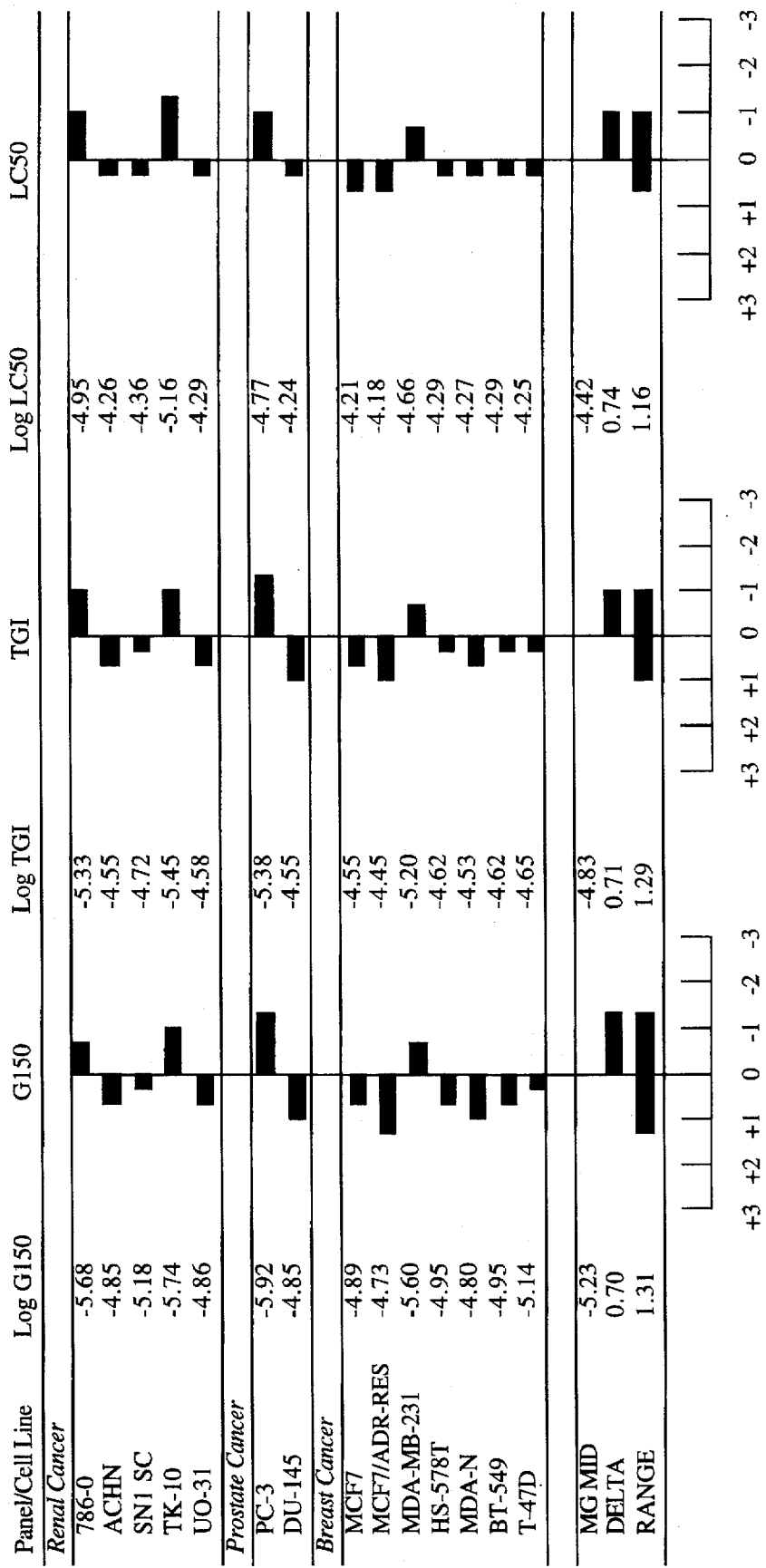

FIGS. 6A, 6B, and 6C depict a mean graph from NCI anti-tumor/anti-cancer screening for the compound 1-O-hexadecyl-2-(1-imidazolyl)-2-deoxy-glycero-3-phosphocholine (CPR 1008).

In each mean graph, a mean of the logarithms of the concentrations of the compound, to which the mean graph corresponds, that produces a particular level of response (e.g., GI50, TGI, or LC50) for all the cell lines in the screen forms the anchor point. The individual response of each cell line to the compound is then depicted by a bar graph either to the right or left of the mean, as previously explained. The notations GI50, TGI, and LC50 refer to the concentrations of the compound in the assay that produces 50% growth inhibition, total growth inhibition, or 50% cell death, respectively.

From the data in FIGS. 1–6, it is evident that the Formula I compounds demonstrate marked anti-tumor activity against a broad range of human tumor cell lines, particularly against breast, colon and leukemia lines. In view of such activity, the Formula I compounds (and pharmaceutically acceptable salts thereof) are active against a wide spectrum of mammalian (including human) tumors and cancerous growths such as cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix, uterus, corpus endometrium, ovary, prostate, testes, bladder, kidney and other urinary tissues, eye, brain and central nervous system, thyroid and other endocrine glands, leukemias (lymphocytic, granulocytic, monocytic), Hodgkin's disease, non-Hodgkin's lymphomas, multiple myeloma, etc. Herein the terms "tumor", "cancer" and "cancerous growths" are used synonymously.

This invention thus provides a method of treating a tumor in a mammal afflicted with same comprising administering to said mammal an anti-tumor-effective amount of a Formula I compound or a pharmaceutically acceptable salt thereof.

Also, then, the invention provides pharmaceutical compositions comprising an anti-tumor-effective amount of a Formula I compound, or a pharmaceutically acceptable salt thereof, and a pharmaceutically acceptable carrier.

B. ANTI-PSORIASIS

Psoriasis is a chronic inflammatory dermatosis characterized, in part, by hyperproliferation of keratinocytes and release of pro-inflammatory cytokines. Compounds that reduce hyperproliferation of keratinocytes in vitro are therefore likely to have utility in the control of psoriasis. The PAM-212 cell line is a keratinocyte line that was isolated and cultivated from newborn BALB/c mice (see S. H. Yuspa et al., Cancer Research, 40, 4694–4703, December, 1980) and is now readily available to the skilled in the art. The cells of the PAM-212 line appear to retain many characteristics of normal keratinocytes. As shown hereinafter, Formula I compounds markedly inhibit proliferation of these cells in vitro, thus indicating their usefulness (and that of their pharmaceutically acceptable salts) in treating psoriasis.

ASSAY

1. Cell line: PAM-212 murine keratinocyte cell line described in S. H. Yuspa, supra.

2. Culture medium: 1:1 DMEM and Ham's F-12 with 10% FBS.

3. Culture conditions are the same as those described hereinabove in parts 3(a) and 3(c) of the assay protocol for anti-tumor activity.

4. Methodology is the same as that described hereinabove in part 4 of the assay protocol for anti-tumor activity, except that, with reference to part 4(f) of the assay protocol for anti-tumor activity, incubation in this case is conducted for 72 hours (rather than 48 hours) under standard culture conditions prior to end point determination.

5. End point determination and analysis is as described hereinabove in part 5 of the assay protocol for anti-tumor activity.

Figure 7:
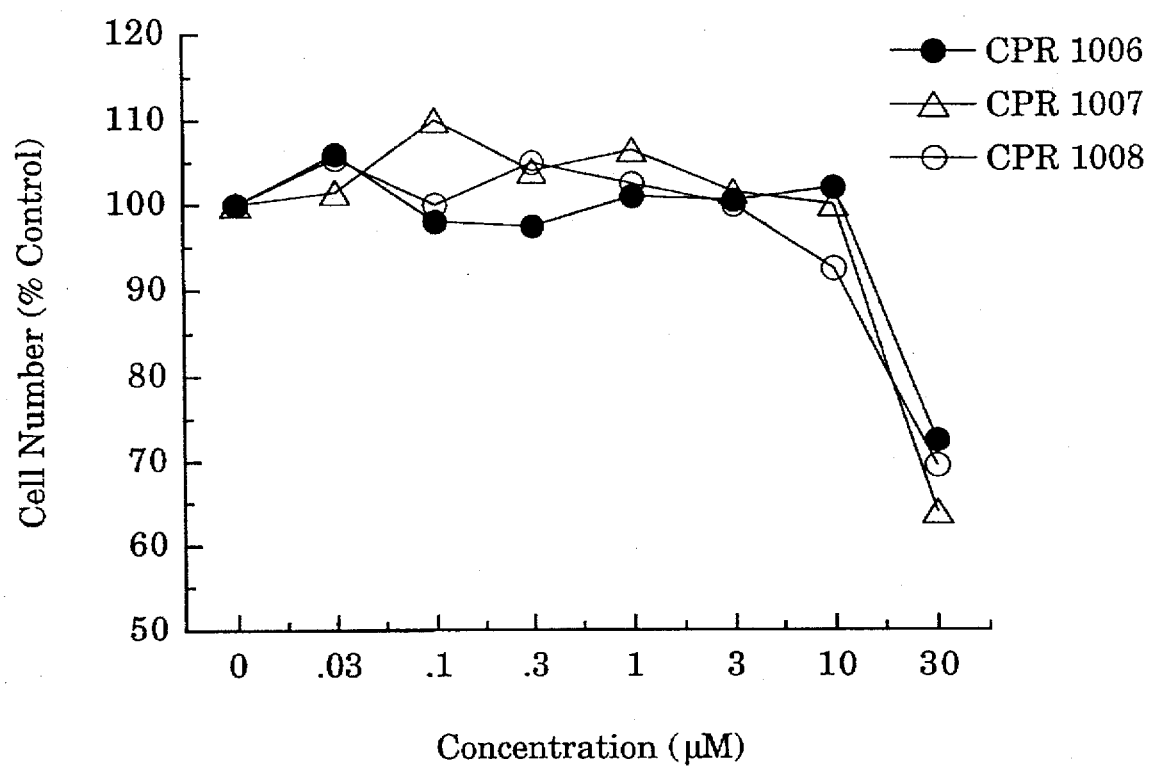
FIG. 7 is a graphical representation of results from an in vitro PAM-212 cell inhibition assay of three compounds of the invention, designated CPR 1006, CPR 1007, and CPR 1008.

6. The results are represented in FIG. 7, which illustrates the marked keratinocyte-proliferation inhibition, and consequently anti-psoriatic activity, at concentrations above 10 μM of Formula I compounds of the invention (and pharmaceutically acceptable salts thereof).

The instant invention thus provides a method of treating psoriasis in a mammal afflicted with same comprising administering to said mammal an anti-psoriatic-effective amount of a Formula I compound or a pharmaceutically acceptable salt thereof. The invention also provides pharmaceutical compositions comprising an anti-psoriatic-effective amount of a Formula I compound (or a pharmaceutically acceptable salt thereof) and a pharmaceutically acceptable carrier.

C. ANTI-INFLAMMATORY

Inflammation is a complex process, involving a variety of cell types including macrophages. See, for example, S. L. Kunkel, "Inflammatory Cytokines", pp. 1–15, in Manual of Vascular Mediators, P. A. Ward, Editor, produced by the publishers of Hospital Practice. References relative to macrophages are numerous, including, for example, J. Immunology 119:950–954 (1977) and Cell 15: 261–267 (1978).

Macrophages are activated by infection and a wide variety of non-infectious irritants and proinflammmatory agents. Upon activation, macrophages participate in a variety of reactions. They may phagocytize bacteria and kill them by either oxygen-dependent or oxygen-independent pathways. They are activated to increase oxygen consumption and production of reactive oxygen species (for example, superoxide). In addition, they release a variety of inflammatory cytokines, including several interleukins and tumor necrosis factor α (TNFα). Inhibition of any of these pathways can lead to reduced inflammation.

The RAW 264.7 cell line (ATCC TIB 71) is a murine monocyte/macrophage line the cells of which show many of the differentiative functions of a macrophage. The cells are capable of phagocytosis and undergo an oxidative burst in response to signals that occasion an oxidative burst in macrophages. Agents that inhibit the activation of cells of the RAW 264.7 line in vitro are therefore inhibitors of critical steps in inflammatory processes.

CHEMILUMINESCENCE (CL) ASSAY—BACKGROUND

Activation of macrophages and other phagocytic cell types initiates a cascade of actions that include increased oxygen consumption (respiratory burst) and production of oxygen radicals. These events can be measured in a variety of ways, including chemiluminescence based on the addition of luminol (see M. A. Trush et al, 1978, The generation of chemiluminescence by phagocytic cells. Methods in Enzymology 57: 462–494). Because chemiluminescence is induced by the increased production of oxygen radicals, that are thought to be important in intracellular killing of bacteria, chemiluminescence has long been used as an index of phagocytic cell activity. In addition, oxygen radical production is associated with inflammatory responses and may have adverse consequences in inflammation that is not due to infection (non-infectious inflammation). For this reason, oxygen radical production associated with macrophage activation is of critical importance in studies of the inflammatory process. Agents that reduce macrophage activation are likely to have utility as anti-inflammatory agents. Since luminesence generated from luminol is a recognized marker of macrophage activation (due to the associated production of oxygen radicals), the finding that Formula I compounds of the present invention (and pharmaceutically acceptable salts thereof) strongly inhibit chemiluminesence in macrophages correlates to the usefulness of these compounds (and salts) in ameliorating inflammation.

ASSAY

Figure 8:
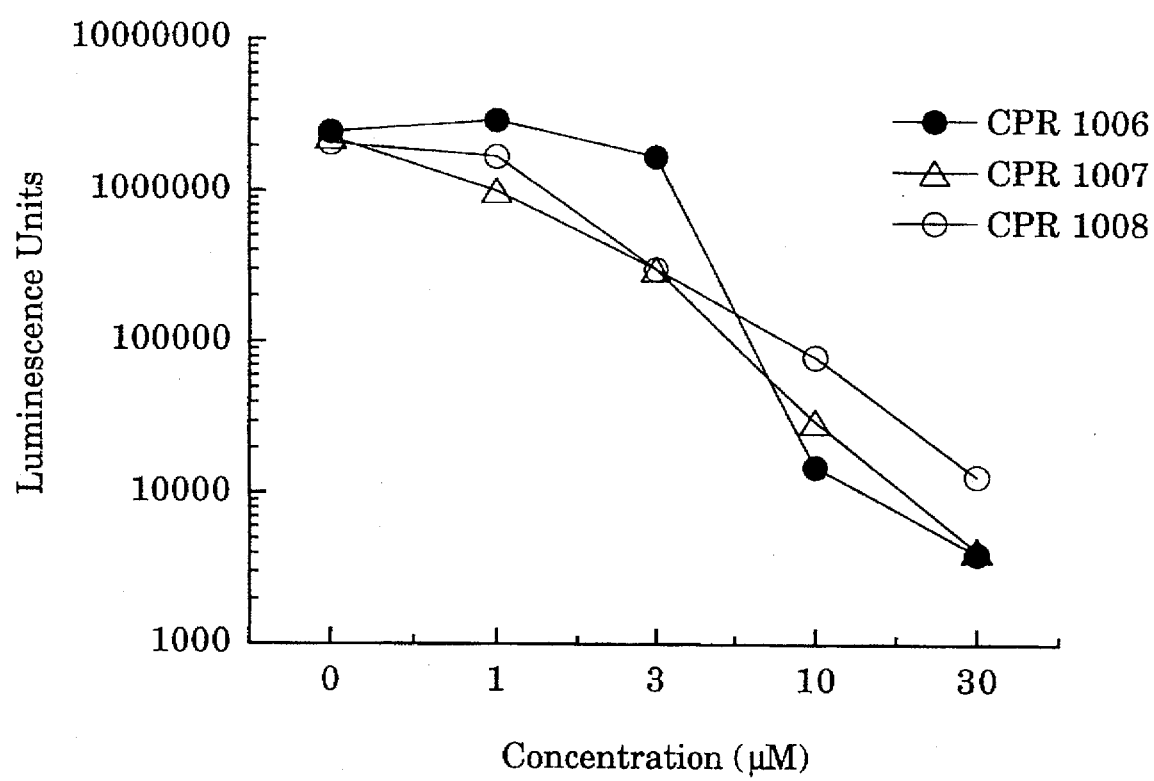
FIG. 8 is a graphical representation of results from an in vitro RAW 264.7 cell macrophage inhibition chemiluminescence assay of three compounds of the invention, designated CPR 1006, CPR 1007 and CPR 1008.

1. Cell line: RAW 264.7 (ATCC TIB 71);

2. Culture medium: DMEM with 10% FBS (attachment dependent);

3. Standard protocol for culturing cell lines: in T-75 or T-150 flasks; 37° C.; 95% air, 5% $CO_2$; 100% humidity;

4. Cell lines are passaged when approximately 80% confluent; with trypsin (1 mg/mL) and EDTA (1 mM EDTA in Ca-Mg free Hank's balanced salt solution); at a 1:4 to 1:5 split;

5. Trypsinize the cells and count with a hemocytometer;

6. Adjust concentration of cells to approximately 1,000,000 cells per mL;

7. Suspend cells in DMEM lacking phenol red and without FBS;

8. Pipette 1 mL of cells into a standard luminometer cuvet (12×75), commercially obtainable from Analytical Luminescence Laboratories, San Diego, Calif., USA;

9. Add luminol to final concentration of 1 µM;

10. Add test compound (0, 1, 3, 10, 30 µM);

11. After 2 minutes, add 100 nanograms of phorbol myristate acetate (PMA);

12. Wait 1 minute and read photo counts (i.e., luminescence) on a Monolight 2010 luminometer available from Analytical Luminescence Laboratories, San Diego;

13. The results are represented in FIG. 8, which illustrates the marked decrease in measured luminescence units by the compounds tested at concentrations above 3 µM.

14. The results are also represented in Table 1, which tabulates the measured cell counts at the indicated concentration of tested compound.

TABLE 1

| Concentration (µM) | Luminescence Units | | |
|---|---|---|---|
| | CPR 1006 | CPR 1007 | CPR 1008 |
| 0 | 2,590,848 | 2,414,436 | 2,182,532 |
| 1 | 2,957,236 | 1,063,719 | 1,749,777 |
| 3 | 1,738,755 | 322,449 | 333,006 |

TABLE 1-continued

| Concentration (µM) | Luminescence Units | | |
|---|---|---|---|
| | CPR 1006 | CPR 1007 | CPR 1008 |
| 10 | 12,988 | 30,452 | 77,061 |
| 30 | 4,660 | 5,095 | 11,654 |

The instant invention thus provides a method of treating inflammation in a mammal afflicted with same comprising administering to said mammal an anti-inflammatory-effective amount of a Formula I compound or a pharmaceutically acceptable salt thereof. The invention also provides pharmaceutical compositions comprising an anti-inflammatory-effective amount of a Formula I compound, or a pharmaceutically acceptable salt thereof, and a pharmaceutically acceptable carrier.

FORMULATIONS

Formulations of the present invention, for medical use, comprise an active compound, i.e., a Formula I compound or a pharmaceutically acceptable salt thereof, together with an acceptable carrier therefor and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a Formula I compound together with a pharmaceutically acceptable carrier thereof.

The formulations include those suitable for oral, rectal or parenteral (including subcutaneous, intramuscular and intravenous) administration. Preferred are those suitable for oral or parenteral administration. Topical formulations are also included, for, for example, anti-psoriatic usage.

It is noted that the Formula I compounds have relatively low melting points which, accordingly, may need to be taken into consideration in, for example, preparing tablets on a commercial scale where the heat of compression may be a factor. The Formula I compounds are also rather insoluble in water and, accordingly, liquid formulations which account for this factor may be made according to art-recognized pharmaceutical techniques, for example, administration dispersed in water as micelles, an injectable wherein the active compound is dissolved in a suitable solvent or co-solvent such as an appropriate polyethylene glycol, or a propylene glycol or the like, or a sealed gelatin capsule enclosing an oily solution of the active compound, or a suppository of the active compound in a conventional suppository base such as cocoa butter, or a liposome formulation, for example, the active compound and a glycerophospholipid such as phosphatidylcholine.

In any event, the aforementioned characteristics of the Formula I compounds are not uncommon in the pharmaceutical area and, accordingly, art-recognized pharmaceutical techniques are employed to prepare appropriate formulations for such compounds as those of Formula I or pharmaceutically acceptable salts thereof.

The formulations may conveniently be presented in unit dosage form and may be prepared by any of the methods well known in the art of pharmacy. All methods include the step of bringing the active compound into association with a carrier which constitutes one of more accessory ingredients. In general, the formulations are prepared by uniformly and inimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as a suspension, solution, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

Formulations suitable for parenteral administration conveniently comprise a sterile preparation of the active compound in, for example, a polyethylene glycol 200 or propylene glycol solution which is preferably isotonic with the blood of the recipient. Liposomes would also provide a convenient formulation.

Useful formulations also comprise concentrated solutions or solids containing the compound of Formula I which upon dilution with an appropriate solvent give a solution suitable for parenteral administration.

Preparations for topical or local applications, which are, for example, conventional for anti-psoriatic usage, comprise aerosol sprays, lotions, gels, ointments, etc. and pharmaceutically acceptable vehicles therefore such as, for example, lower aliphatic alcohols, polyglycerols such as glycerol, polyethyleneglycerol, esters of fatty acids, oils and fats, silicones, and other conventional topical carriers. Again, liposomes provide a convenient formulation.

In topical formulations, the compounds of Formula I are preferably utilized at concentrations of from about 0.1% to about 5.0% percent by weight.

In addition to the aforementioned ingredients, the formulations of this invention may further include one or more optional accessory ingredient(s) utilized in the art of pharmaceutical formulations, e.g., diluents, buffers, flavoring agents, binders, surface active agents, thickeners, lubricants, suspending agents, preservatives (including antioxidants) and the like.

The amount of compound of Formula I required to be effective for the indicated activity will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective dose is in the range of about 0.1 to about 200 mg/kg body weight per day, preferably in the range of about 1 to about 100 mg/kg per day. The total daily dose may be given as a single dose, multiple doses, e.g., two to six times per day, or by intravenous infusion for a selected duration. Dosages above or below the range cited above are within the scope of the present invention and may be administered to the individual patient if desired and necessary.

For example, for a 75 kg mammal, a dose range would be about 75 to about 7500 mg per day, and a typical dose would be about 800 mg per day. If discrete multiple doses are indicated, treatment might typically be 200 mg of a compound of Formula I given 4 times per day.

The following examples are intended to illustrate and not to limit the scope of the present invention. Examples 1–8 are illustrative of Reaction Scheme 1; examples 9–17 are illustrative of Reaction Scheme 2; examples 18–26 are illustrative of Reaction Scheme 3; and examples 27–31 are illustrative of Reaction Scheme 4.

EXAMPLE 1

A. 1-O-Octadecyl-2-O-p-Toluenesulfonyl-3-O-Trityl-Glycerol

A solution of 1-O-octadecyl-3-O-trityl-glycerol (173.51 g, 295.63 mmol) in 895 mL water-free pyridine is added dropwise to a solution of p-toluenesulfonyl chloride (88.49 g, 464.15 mmol) in 670 mL water-free pyridine with constant stirring. The reaction mixture is kept at ambient temperature (20°–23° C.) for two days. Diethyl ether ($Et_2O$) (2.8 L) is added and the organic phase is washed six times with water, twice with 0.5N HCl (500 mL each), twice with diluted aqueous sodium carbonate, and then washed with water until neutral. After drying the organic phase over sodium sulfate, the solvent is removed under vacuum. The residue is triturated with isopropanol (1140 mL) with stirring until the product crystallizes. After cooling to 4° C., the product, 1-O-octadecyl-2-O-p-toluenesulfonyl-3-O-trityl-glycerol, is isolated by filtration, washed with isopropanol and dried under vacuum. Yield: 190.14 g (86.91%); m.p. 56°–58° C.; Rf value (TLC on silica gel 60) of 0.38 with benzene as the developing solvent; and Rf of 0.74 with benzene/methanol (50/2).

B. By following the procedure of Example 1-A, except that an equivalent amount of 1-O-hexadecyl-3-O-trityl-glycerol is utilized as the starting Formula (A) Compound, there is obtained as final product the corresponding 1-O-hexadecyl-2-O-p-toluenesulfonyl-3-O-trityl-glycerol; yield 73%; Rf value: 0.37 benzene; 0.79 benzene/methanol (50/2).

EXAMPLE 2

The procedure of Example 1-A is followed except that an equivalent amount of the appropriate 1-O-R-3-O-trityl-glycerol is utilized as the starting Formula (A) compound to yield the following respective Formula (B) compounds:

a. 1-O-eicosyl-2-O-p-toluenesulfonyl-3-O-trityl-glycerol;
b. S-1-O-octadecyl-2-O-p-toluenesulfonyl-3-O-trityl-glycerol;
c. 1-O-(1-methylheptadecyl)-2-O-p-toluenesulfonyl-3-O-trityl-glycerol;
d. 1-O-tetradecyl-2-O-p-toluenesulfonyl-3-O-trityl-glycerol;
e. R-1-O-hexadecyl-2-O-p-toluenesulfonyl-3-O-trityl-glycerol;
f. 1-O-(cis-9-octadecenyl)-2-O-p-toluenesulfonyl-3-O-trityl-glycerol; and
g. 1-O-(trans-8-hexadecenyl)-2-O-p-toluenesulfonyl-3-O-trityl-glycerol.

EXAMPLE 3

A. 1-O-Octadecyl-2-(1-Imidazolyl)-2-Deoxy-3-O-Trityl-Glycerol

1-O-octadecyl-2-p-toluenesulfonyl-3-O-trityl-glycerol (106.56 g, 144 mmol) and imidazole (29.28 g, 430 mmol) are dissolved in water-free dimethyl sulfoxide (800 mL) at 100° C. A solution of sodium dimethylsulfinylmethide, prepared from metallic sodium (6.72 g) in 800 mL dimethyl sulfoxide, is added and the resultant mixture is stirred at 100° C. for 72 hours. After cooling, diethyl ether (2000 mL) is added. The organic phase is washed six times with water (1500 mL each) and dried over sodium sulfate. The solvent is removed under vacuum.

The thus-obtained crude product (87.6 g), consisting of starting material and the desired product, according to thin layer chromatography (TLC) analysis, is purified by medium pressure liquid chromatography (MPLC). A solution of the crude product (0.6 g) in methylene chloride (2.0 mL) is applied onto a MPLC-column (30×3 cm) filled with silica gel 35–70 with the following parameters: pressure-0.9 atmosphere; flow rate-500 mL/hour; solvent--methylene chloride (fractions 1–35) and methylene chloride/methanol (40/2 v/v); fraction volumes of 10–15 mL are collected; yield is about 60%; purified 1-O-octadecyl-2-(1-imidazolyl) -2-deoxy-2-deoxy-3-O-trityl-glycerol; m.p. 53°–58° C.; Rf value: 0.30 benzene/methanol 50/5.

MPLC purification of a larger amount of the crude product (1.85 g) in 3 mL methylene chloride/diethyl ether (40/2.5 v/v) is also carried out using a 40×4 cm column (pressure-0.9 atmosphere, flow rate-700 mL/hr).

B. The procedure of Example 3-A is followed, except that an equivalent amount of 1,2,4-triazole is substituted for the imidazole used therein, to yield as final product (oily liquid) the corresponding 1-O-octadecyl-2-(1-triazolyl)-2-deoxy-3-O-trityl-glycerol; Rf value: 0.31 methylene chloride/ether 3/1; yield 83% after purification by column chromatography.

C. By following the procedure of Example 3-A, except that an equivalent amount of 1-O-hexadecyl-2-O-p-toluenesulfonyl-3-O-trityl-glycerol is utilized as the starting Formula (B) compound, there is obtained as final product the corresponding 1-O-hexadecyl-2-(1-imidazolyl)-2-deoxy-3-O-trityl-glycerol; Rf value: 0.29 toluene/methanol 50/3; yield 45% after purification by column chromatography.

EXAMPLE 4

The procedure of Example 3-A is followed except that an equivalent amount each of the appropriate Formula (B) compound and the appropriate Het-Compound is utilized as the initial reactants to yield the following respective Formula (C) compounds as final products:

a. 1-O-eicosyl-2-(1-imidazolyl)-2-deoxy-3-O-trityl-glycerol;

b. S-1-O-octadecyl-2-(1-imidazolyl)-2-deoxy-3-O-trityl-glycerol;

c. 1-O-(1-methylheptadecyl)-2-pyrrolyl-2-deoxy-3-O-trityl-glycerol;

d. 1-O-tetradecyl-2-benztriazolyl-2-deoxy-3-O-trityl-glycerol;

e. R-1-O-hexadecyl-2-(1-imidazolyl)-2-deoxy-3-O-trityl-glycerol;

f. 1-O-(cis-9-octadecenyl)-2-pyrazolyl-2-deoxy-3-O-trityl-glycerol; and g. 1-O-(trans-8-hexadecenyl)-2-indolyl-2-deoxy-3-O-trityl-glycerol.

EXAMPLE 5

A. 1-O-Octadecyl-2-(1-Imidazolyl)-2-Deoxy-Glycerol

A solution of boron trifluoride (50%) in methanol (88 mL) is added to a solution of 1-O-octadecyl-2-(1-imidazolyl)-2-deoxy-3-O-trityl-glycerol (87.6 g, 137.52 mmol) in methylene chloride (2000 mL) and the resultant dark green solution is kept at ambient temperature for 24 hours. After washing with water (500 mL) the color changes to yellow. The resulting emulsion is separated into two phases by the addition of sodium chloride. The organic phase is washed consecutively with diluted aqueous sodium carbonate and water until neutral. After drying over sodium sulfate, the solvent is removed under vacuum. The thus-obtained crude 1-O-octadecyl-2-(1-imidazolyl)-2-deoxy-glycerol is purified by column chromatography as follows:

column: Prep 500 silica (Waters Chromatography, Milford, Mass., USA);

solvent: methylene chloride/methanol/conc. ammonia 40/3.5/0.1 v/v/v;

pressure: 13 bar;

flow rate: 200–250 mL/hr;

yield: 19.3 g (68%);

m.p.: 56°–58° C.;

Rf value: 0.21 $CH_2Cl_2/CH_3OH/c.$ $NH_3$ 40/3.5/0.1 v/v/v; 0.38 benzene/methanol 45/5 v/v.

Note: The workup procedure might be improved with 4N sodium hydroxide (about 10% excess) added directly to the reaction mixture with stirring, followed by washing the organic phase until neutral.

B. By following the procedure of Example 5-A, except that an equivalent amount each of the 2-(1-triazolyl) and the 2-(1-imidazolyl) derivatives from Examples 3-B and 3-C, respectively, is utilized as the starting Formula (C) compound, the following respective final products are obtained:

1-O-octadecyl-2-(1-triazolyl)-2-deoxy-glycerol; m.p. 73°–78° C.; Rf value: 0.42 (methylene chloride/ methanol 45/5); 0.13 (benzene/methanol 50/5); yield 83% after purification by column chromatography; and 1-O-hexadecyl-2-(1-imidazolyl)-2-deoxy-glycerol; m.p. 52°–56° C.; Rf value: 0.50 methylene chloride/ methanol/water 40/15/1.5; yield 79% after purification by column chromatography.

EXAMPLE 6

The procedure of Example 5-A is followed, except that an equivalent amount each of the Formula (C) compounds from Example 4 is substituted for the 1-O-octadecyl-2-(1-imidazolyl)-2-deoxy-3-O-trityl-glycerol of Example 5-A, to yield the following respective Formula (D) compounds:

a. 1-O-eicosyl-2-(1-imidazolyl)-2-deoxy-glycerol;

b. S-1-O-octadecyl-2-(1-imidazolyl)-2-deoxy-glycerol;

c. 1-O-(1-methylheptadecyl)-2-pyrrolyl-2-deoxy-glycerol;

d. 1-O-tetradecyl-2-benztriazolyl-2-deoxy-glycerol;

e. R-1-O-hexadecyl-2-(1-imidazolyl)-2-deoxy-glycerol;

f. 1-O-(cis-9-octadecenyl)-2-pyrazolyl-2-deoxy-glycerol; and g. 1-O-(trans-9-hexadecenyl)-2-indolyl-2-deoxy-glycerol.

EXAMPLE 7

A. 1-O-Octadecyl-2-(1-Imidazolyl)-2-Deoxy-Glycero-3-Phosphocholine 3.95 Grams (10 mmol) of 1-O-octadecyl-2-(1-imidazolyl) -2-deoxy-glycerol is dissolved in water-free toluene (150 mL). After removal of 25 mL solvent under vacuum, triethylamine (1.16 g, 11.5 mmol) in dry toluene (20 mL) is added slowly with stirring, followed by dropwise addition of a solution of 2-chloro-2-oxo-1,3,2-dioxaphospholane (1.58 g, 11 mmol) in 20 mL toluene. (Note: 2-chloro-2-oxo-1,3, 2-dioxaphospholane is not stable under storage and decomposes if heated.) The reaction mixture is stirred for 24 hours. Two additional portions of 0.58 g and 0.79 g triethylamine dissolved in toluene (15 mL each) are added after 24 and 48 hours, respectively. The resultant precipitate of triethylamine hydrochloride is removed by filtration and washed with toluene.

The filtered organic solvent is removed under vacuum and the residue is triturated in a pressure bottle with 130 mL dry acetonitrile. After addition of 12 g dry trimethylamine, the resultant reaction mixture is stirred at 60° C. for 24 hours (use round bottom flask and fix glass stopper by a mechanical device). After cooling to 0° C., the resultant precipitate is separated by filtration followed by consecutive washing with acetonitrile and acetone. Residual solvent is removed under vacuum. Yield of crude 1-O-octadecyl-2-(1-imidazolyl)-2-deoxy-glycero-3-phosphocholine: 5.54 g (98.86%), which is purified as follows:

Purification by column chromatography:

A solution of the crude product (5.4 g) in 7 mL methylene chloride/methanol (7/3, v/v) is applied onto a column Prep 500 silica (Waters Chromatography);
pressure: 23 bar;
flow rate: 200 mL/min;
solvent: methylene chloride/methanol/2N ammonia (40/30/6, v/v/v);
yield: 57%;
Rf value: 0.19 $CH_2Cl_2/CH_3OH$/c. $NH_3$(40/30/6, v/v/v).

Further purification:
The product is dissolved in ethanol (15 mL) and the resultant solution is passed over alumina (10 g, coarse, not for column chromatography).

B. By following the procedure of Example 7-A, except that an equivalent amount each of the 2-(1-triazolyl) and the 2-(1-imidazolyl) derivatives from Example 5-B is utilized as the starting Formula (D) compound, the following respective final products are obtained:

1-O-octadecyl-2-(1-triazolyl)-2-deoxy-glycero-3-phosphocholine; Rf value: 0.17 $CH_2Cl_2/CH_3OH$/c. $NH_3$ 40/30/6; yield 23% after purification by column chromatography; and 1-O-hexadecyl-2-(1-imidazolyl)-2-deoxy-glycero-3-phosphocholine; Rf value: 0.18 $CH_2Cl_2/CH_3OH$/c. $NH_3$ 40/30/6; yield 37% after purification by column chromatography.

C. The compounds, 1-O-octadecyl-2-(1-imidazolyl)-2-deoxy-glycero-3-phospho-(N-methyl)-ethanolamine and the corresponding -3-phospho-(N,N-dimethyl)-ethanolamine, are each prepared in a manner analogous to that described for the -3-phosphocholine of Example 7-A, except that an equivalent amount each of methylamine and dimethylamine, respectively, is substituted for the trimethylamine used therein.

EXAMPLE 8

The procedure of Example 7-A is followed, except that an equivalent amount each of the Formula (D) compounds from Example 6 is substituted for the 1-O-octadecyl-2-(1-imidazolyl)-2-deoxy-glycerol of Example 7-A, to yield the following respective Formula (E) compounds:

a. 1-O-eicosyl-2-(1-imidazolyl)-2-deoxy-glycero-3-phosphocholine;
b. S-1-O-octadecyl-2-(1-imidazolyl)-2-deoxy-glycero-3-phosphocholine;
c. 1-O-(1-methylheptadecyl)-2-pyrrolyl-2-deoxy-glycero- 3-phosphocholine;
d. 1-O-tetradecyl-2-benztriazolyl-2-deoxy-glycero-3-phosphocholine;
e. R-1-O-hexadecyl-2-(1-imidazolyl)-2-deoxy-glycero-3-phosphocholine;
f. 1-O-(cis-9-octadecenyl)-2-pyrazolyl-2-deoxy-glycero-3-phosphocholine; and
g. 1-O-(trans-9-hexadecenyl)-2-indolyl-2-deoxy-glycero-3-phosphocholine.

EXAMPLE 9

1-O-Octadecyl-2-Benzoyl-3-O-p-Toluenesulfonyl-Glycerol 9.98 Grams (20 mmol) of Compound (F), with R being $C_{18}H_{37}$, is dissolved in 150 mL dry toluene. 3.88 grams (30 mmol) of diisopropyl-ethylamine is added followed by a solution of 4.19 g (30 mmol) of benzoic acid chloride in 50 mL toluene within 10 minutes. The clear reaction mixture is allowed to stand 48 hours at room temperature, washed with water, washed twice with saturated sodium bicarbonate solution, again with water, dried over sodium sulfate, filtered and evaporated to dryness. The residual waxy solid (12.2 g) of 1-O-octadecyl-2-benzoyl-3-O-p-toluenesulfonyl-glycerol is used without further purification in the succeeding step.

EXAMPLE 10

The procedure of Example 9 is followed, except that an equivalent amount of the appropriate Formula (F) compound is utilized as the initial reactant, to yield the following respective Formula (G) compounds:

a. 1-O-tetradecyl-2-benzoyl-3-O-p-toluenesulfonyl-glycerol;
b. 1-O-hexadecyl-2-benzoyl-3-O-p-toluenesulfonyl-glycerol;
c. 1-O-eicosyl-2-benzoyl-3-O-p-toluenesulfonyl-glycerol;
d. S-1-O-octadecyl-2-benzoyl-3-O-p-toluenesulfonyl-glycerol: and
e. R-1-O-hexadecyl-2-benzoyl-3-O-p-toluenesulfonyl-glycerol.

EXAMPLE 11

A. 1-O-Octadecyl-2-Benzoyl-3-(1-Triazolyl)-3-Deoxy-Glycerol 12.2 grams (approximately 20 mmol) of the waxy solid obtained in Example 9 is reacted with the Het-Compound, triazole, under the same reaction conditions and molar ratios as described for Step 2 of Reaction Scheme 1. After purification by column chromatography (400 g silica gel; toluene as the mobile phase), about 5.37 g (53.73% theoretical yield) of 1-O-octadecyl-2-benzoyl-3-(1-triazolyl)-3-deoxy-glycerol is obtained: Rf value of 0.65; silica gel;methylene chloride/methanol 45/5.

EXAMPLE 12

By following the procedure of Example 11, except that an equivalent amount each of the appropriate Formula (G) compound of Example 10 and the appropriate Het-Compound is utilized as the initial reactants, the following respective final products of Formula (H) are obtained:

a. 1-O-tetradecyl-2-benzoyl-3-(1-imidazolyl)-3-deoxy-glycerol;
b. 1-O-hexadecyl-2-benzoyl-3-(1-triazolyl)-3-deoxy-glycerol;

c. 1-O-eicosyl-2-benzoyl-3-pyrrolyl-3-deoxy-glycerol;

d. S-1-O-octadecyl-2-benzoyl-3-benztriazolyl-3-deoxy-glycerol;

e. R-1-O-hexadecyl-2-benzoyl-3-indolyl-3-deoxy-glycerol;

f. 1-O-(9-octadecenyl)-2-benzoyl-3-pyrazolyl-3-deoxy-glycerol; and g. 1-O-(9-hexadecenyl)-2-benzoyl-3-(1-triazolyl)-3-deoxy-glycerol.

EXAMPLE 13

1-O-Octadecyl-2-Hydroxy-3-(1-Triazolyl)-3-Deoxy-Glycerol 5.0 Grams (10 mmol) of 1-O-octadecyl-2-benzoyl-3-(1-triazolyl)-3-deoxy-glycerol is dissolved in 100 mL ethanol and 5 mL of 4N sodium hydroxide (20 mmol) in water is added at one time and allowed to stand overnight at room temperature. The ethanol is then removed under reduced pressure. 50 mL of 0.2N acetic acid in water and 150 mL toluene are then added. The phases are separated and the toluene phase is washed two times with 50 mL water, dried over sodium sulfate and brought to dryness. The semisolid residue (3.82 g, 96.56% theoretical) of 1-O-octadecyl-2-hydroxy-3-(1-triazolyl)-3-deoxy-glycerol shows one spot in TLC; Rf=0.39, silica gel, methylene chloride/methanol 45/5, and is utilized in the succeeding step without further purification.

EXAMPLE 14

Saponification of each of the Formula (H) compounds of Example 12 in accordance with the teaching of Example 13 yields the following respective compounds of Formula (J):

a. 1-O-tetradecyl-2-hydroxy-3-(1-imidazolyl)-3-deoxy-glycerol;

b. 1-O-hexadecyl-2-hydroxy-3-(1-triazolyl)-3-deoxy-glycerol;

c. 1-O-eicosyl-2-hydroxy-3-pyrrolyl-3-deoxy-glycerol;

d. S-1-O-octadecyl-2-hydroxy-3-benztriazolyl-3-deoxy-glycerol;

e. R-1-O-hexadecyl-2-hydroxy-3-indolyl-3-deoxy-glycerol;

f. 1-O-(9-octadecenyl)-2-hydroxy-3-pyrazolyl-3-deoxy-glycerol; and 9. i-o-(9-hexadecenyl)-2-hydroxy-3-(1-triazolyl)-3-deoxy-glycerol.

EXAMPLE 15

1-O-Octadecyl-3-(1-Triazolyl)-3-Deoxy-Glycero-2-Phosphocholine

The procedure of Step 4 of Reaction Scheme 1 is followed, reacting 1.88 g (5 mmol) of the Formula (J) compound, 1-O-octadecyl-2-hydroxy-3-(1-triazolyl)-2-deoxy-glycerol, under the same reaction conditions and molar ratios, with 2-chloro-2-oxo-1,3,2-dioxaphospholane and subsequently with trimethylamine. Working up and purification by column chromatography yields 0.82 g (29.24% theoretical) of the pure compound, 1-O-octadecyl-3-(1-triazolyl)-3-deoxy-glycero-2-phosphocholine; Rf=0.20, silica gel, CH$_2$Cl$_2$/CH$_3$OH/c. NH$_3$ 40/30/6.

EXAMPLE 16

By following the procedure of Example 15, except that an equivalent amount each of methylamine and dimethylamine is substituted for the trimethylamine used therein, the respective compounds, 1-O-octadecyl-3-(1-triazolyl)-3-deoxy-glycero-2-phospho- (N-methyl)-ethanolamine and 1-O-octadecyl-3-(1-triazolyl)-3-deoxy-glycero-2-phospho (N,N-dimethyl)ethanolamine are obtained.

EXAMPLE 17

The procedure of Example 15 is followed, except that an equivalent amount of each Formula (J) compound of Example 14 is utilized as the initial reactant, to yield the following respective Formula (K) compounds:

a. 1-O-tetradecyl-3-(1-imidazolyl)-3-deoxy-glycero-2-phosphocholine;

b. 1-O-hexadecyl-3-(1-triazolyl)-3-deoxy-glycero-2-phosphocholine;

c. 1-O-eicosyl-3-pyrrolyl-3-deoxy-glycero-2-phosphocholine;

d. S-1-O-octadecyl-3-benztriazolyl-3-deoxy-glycero-2-phosphocholine;

e. R-1-O-hexadecyl-3-indolyl-3-deoxy-glycero-2-phosphocholine;

f. 1-O-(9-octadecenyl)-3-pyrazolyl-3-deoxy-glycero-2-phosphocholine; and g. 1-O-(9-hexadecenyl)-3-(1-triazolyl)-3-deoxy-glycero-2-phosphocholine.

EXAMPLE 18

1-Bromo-1-Deoxy-2-O-Octadecyl-3-Benzoyl-Glycerol 8.65 Grams (20 mmol) of 2-O-octadecyl-1,3-benzylidene-glycerol is reacted with 3.92 g (22 mmol) of N-bromosuccinimide and 8.90 g (40 mmol) of barium carbonate in 100 mL carbon tetrachloride under reflux with stirring for two hours. The reaction mixture is filtered and the filter cake is washed twice with carbon tetrachloride and evaporated to dryness. The residue is taken up in 40 mL of toluene and purified by column chromatography on silica gel with toluene/cyclohexane (3/2) as the mobile phase. Removal of the solvent yields 6.83 g (66.70% theoretical) of pure 1-bromo-1-deoxy-2-O-octadecyl-3-benzoyl-glycerol; Rf=0.21, silica gel, toluene.

EXAMPLE 19

The procedure of Example 18 is followed using an equivalent amount of the appropriate Formula (L) compound as the initial reactant to yield the following respective compounds of Formula (M):

a. 1-bromo-1-deoxy-2-O-tetradecyl-3-benzoyl-glycerol;

b. 1-bromo-1-deoxy-2-O-hexadecyl-3-benzoyl-glycerol;

c. 1-bromo-1-deoxy-2-O-eicosyl-3-benzoyl-glycerol; and d. 1-bromo-1-deoxy-2-O-(9-octadecenyl)-3-benzoyl-glycerol.

EXAMPLE 20

1-[1-(2-Methyl)-Imidazolyl]-1-Deoxy-2-O-Octadecyl-3-Benzoyl-Glycerol

Ten millimols of 1-bromo-1-deoxy-2-O-octadecyl-3-benzoyl-glycerol is reacted with the Het-Compound, 2-methylimidazole, in accordance with the procedure outlined in Example 3 (Step 2 of Reaction Scheme 1) utilizing the same conditions and molar ratios. After completion of the reaction, workup and purification as therein described, about 2.89 g (56.3% theoretical) of the Formula (N) compound, 1-[1-(2-methyl)-imidazolyl]-1-deoxy-2-O- octadecyl-3-benzoyl-glycerol, is obtained; Rf=0.58, silica gel, $CH_2Cl_2/CH_3OH$ 45/5.

EXAMPLE 21

By following the procedure of Example 20, except that an equivalent amount each of the Formula (M) compound of Example 19 and the appropriate Het-Compound are the reactants, the following respective compounds of Formula (N) are obtained:

a. 1-(1-triazolyl)-1-deoxy-2-O-octadecyl-3-benzoyl-glycerol;

b. 1-(1-imidazolyl)-1-deoxy-2-O-hexadecyl-3-benzoyl-glycerol;

c. 1-pyrrolyl-1-deoxy-2-O-tetradecyl-3-benzoyl-glycerol;

d. 1-benztriazolyl-1-deoxy-2-O-eicosyl-3-benzoyl-glycerol; and e. 1-indolyl-1-deoxy-2-O-(9-octadecenyl)-3-benzoyl-glycerol.

EXAMPLE 22

1-[1-(2-Methyl)-Imidazolyl]-1-Deoxy-2-O-Octadecyl-Glycerol

Ten millimols of 1-[1-(2-methyl)-imidazolyl]-1-deoxy-2-O-octadecyl-3-benzoyl chloride is debenzoylated in accordance with the procedure outlined in Example 13 (Step 3 of Reaction Scheme 2) utilizing the same conditions and molar ratios to yield about 4.01 g of the Formula (O) compound, 1-[1-(2-methyl)-imidazolyl]-1-deoxy-2-O-octadecyl-glycerol; Rf=0.37, silica gel, $CH_2Cl_2/CH_3OH$ 45/5.

EXAMPLE 23

Debenzoylation of each Formula (N) compound of Example 21 in accordance with the procedure of Example 22 affords the following respective compounds of Formula (O):

a. 1-(1-triazolyl)-1-deoxy-2-O-octadecyl-glycerol;

b. 1-(1-imidazolyl)-1-deoxy-2-O-hexadecyl-glycerol;

c. 1-pyrrolyl-1-deoxy-2-O-tetradecyl-glycerol;

d. 1-benztriazolyl-1-deoxy-2-O-eicosyl-glycerol; and e. 1-indolyl-1-deoxy-2-O-(9-octadecenyl)-glycerol.

EXAMPLE 24

1-[1-(2-Methyl)-Imidazolyl]-1-Deoxy-2-O-Octadecyl-Glycero-3-Phosphocholine

The procedure of Step 4 of Reaction Scheme 1 is followed, reacting 2.04 g (5 mmol) of the Formula (O) compound, 1-[1-(2-methyl)-imidazolyl]-1-deoxy-2-O-octadecyl-glycerol, under the same reaction conditions and molar ratios, with 2-chloro-2-oxo-1,3,2-dioxaphospholane and subsequently with trimethylamine. Working up and purification by column chromatography yields 0.79 g (27.57% theoretical) of pure 1-[1-(2-methyl)-imidazolyl]-1-deoxy-2-O-octadecyl-glycero-3-phosphocholine as a colorless, crystalline solid; Rf=0.15, silica gel, $CH_2Cl_2/CH_3OH/c. NH_3$ 40/30/6.

EXAMPLE 25

By following the procedure of Example 24, except that an equivalent amount each of methylamine and dimethylamine is substituted for the trimethylamine used therein, the respective compounds, 1-[1-(2-methyl)-imidazolyl]-1-deoxy-2-O-octadecyl-glycero-2-phospho-(N-methyl) ethanolamine and 1-[1-(2-methyl)-imidazolyl]-1-deoxy-2-O-octadecyl-glycero-2-phospho-(N,N-dimethyl)-ethanolamine are obtained.

EXAMPLE 26

The procedure of Example 24 is followed, except that an equivalent amount of each Formula (O) compound of Example 23 is utilized as the initial reactant, to yield the following respective Formula (P) compounds:

a. 1-(1-triazolyl)-1-deoxy-2-O-octadecyl-glycero-3-phosphocholine;

b. 1-(1-imidazolyl)-1-deoxy-2-O-hexadecyl-glycero-3-phosphocholine;

c. 1-pyrrolyl-1-deoxy-2-O-tetradecyl-glycero-3-phosphocholine;

d. 1-benztriazolyl-1-deoxy-2-O-eicosyl-glycero-3-phosphocholine; and e. 1-indolyl-1-deoxy-2-O-(9-octadecenyl)-glycero-3-phosphocholine.

EXAMPLE 27

2-O-Octadecyl-3-O-Trityl-Glycerol

A mixture of 20 g 2-O-octadecylglycerol (58.8 mmol), obtained from conventional acid-catalyzed hydrolysis (HCl/MeOH) of 2-O-Octadecyl-1,3-benzylideneglycerol and 19.6 triphenylchloromethane (70.56 mmol) in 240 ml of anhydrous pyridine is stirred for 48 h at room temperature under anhydrous conditions. The solution is poured into ice-cold water (500 ml), and the mixture is extracted with 3 portions (200 ml each) of light petroleum. The organic phase is washed with water (3×100 ml) and dried over anhydrous sodium sulphate. The solvent is evaporated, and light petroleum (180 ml) is added to the residue. On standing overnight some triphenylmethanol is precipitated. The solid is filtered off, and the filtrate is evaporated to dryness. The crude product, which contains traces of unreacted 2-O-octadecylglycerol and some 1,3-di-O-trityl-2-O-octadecylglycerol, is purified by column chromatography on silica gel using a petroleum ether-diethylether gradient. The yield of pure 2-O-octadecyl-3-O-trityl-,glycerol is 20.5 g (60%).

EXAMPLE 28

1-p-Toluenesulfonyl-2-O-Octadecyl-3-O-Trityl-Glycerol

A solution of 2-O-Octadecyl-3-O-trityl-glycerol (10 g, 17.04 mmol) in 52 ml water-free pyridine is added dropwise during 30 min. to a solution of p-toluenesulfonyl chloride (5.1 g, 26.75 mmol) in 39 ml water-free pyridine under stirring. After 2 days at room temperature 162 ml diethyl ether are added and the precipitate formed is removed by filtration. The organic phase is washed successively with water (6×50 ml), 0.5N HCl (2×29 ml), 0.5N sodium carbonate (2×29 ml), and water (4×50 ml). Evaporation of the solvent under vacuum gives an oily product which becomes solid after drying in vacuo. The product, 1-p-toluenesulfonyl-2-O-Octadecyl-3-O-trityl-glycerol (10.5 g, 85% yield), is used for the next step without further purification.

EXAMPLE 29

1-(1-Imidazolyl)-1-Deoxy-2-O-Octadecyl-3-O-Trityl-Glycerol

The product of Example 28 (10.5 g, 14.1 mmol) and imidazole (2.88 g, 42.3 mmol) are dissolved in water-free dimethyl sulfoxide (80 ml) at 50° C. A solution of sodium dimethylsulfinylmethide, prepared from metallic sodium (0.648 g, 28.2 mg atoms) in 80 ml dimethyl sulfoxide, is added dropwise (over 30 min.) at 50° C. The reaction mixture is stirred at 100° C. (silicon oil bath) for 72 h. After cooling, to room temperature, 210 ml diethyl ether are added and extraction with diethyl ether is repeated with 2×80 ml portions. The ether extracts are combined and washed with water (6×100 ml). The solution is dried over sodium sulfate and the solvent is removed under vacuum. After drying in high vacuum, 8.1 g (90% yield) of crude 1-(1-imidazolyl)-1-deoxy-2-O-octadecyl-3-O-trityl-glycerol are obtained and used in the next step without purification.

EXAMPLE 30

1-(1-imidazolyl)-1-Deoxy-2-O-Octadecyl-Glycerol

To the product of Example 29 (8.1 g, 12.86 mmol) in 200 ml dichloromethane, borontrifluoride (8 ml; 50% $BF_3$ in methanol) is added. The dark green solution is stirred at room temperature for 24 h. Then approximately 22 ml 4N NaOH are added to bring the pH to 9.0. The organic phase is washed with water (5×100 ml) and dried over sodium sulfate. Evaporation of the solvent under vacuum gives 8.5 crude product which is purified by repeated column chromatography on silica gel. First run: column 28×2.8 cm; sequence of solvents:

1. chloroform (100 ml);
2. chloroform-methanol-35% ammonia (100:0.5:0.25; 201.5 ml);
3. chloroform-methanol-35% ammonia (100:4:0.25; 104.25 ml); and
4. chloroform-methanol-35% ammonia (100:8:0.25; 433 ml).

Flow rate 12 ml/min., 15 ml fractions are collected and monitored by TLC, using chloroform-methanol (9:1) as the developing solvent. Fractions 22–29 (solvent 4) are combined and the solvents evaporated to yield 3.5 g of product which is chromatographed on a 20×2 cm column using the same sequence of solvents as for the first chromatography. Fractions 4–29 (solvent 4) are combined and the solvents evaporated to give 2.46 g of 1-(1-imidazoyl)-1-deoxy-2-O-octadecyl-glycerol (50% yield) as a white solid.

EXAMPLE 31

1-(1-Imidazolyl)-2-Deoxy-2-O-Octadecyl-Glycero-3-Phosphocholine

To a solution of 1.1 g of 1-(1-imidazolyl)-1-deoxy-2-O-octadecyl-glycerol (2.78 mmol) and 0.338 (0.463 mmol) triethylamine in 28 ml benzene at 6° C. is added dropwise (during 30 min.) a solution of 0.476 g (0.31 ml, 3.34 mmol) of 2-chloro-2-oxo-1,3,2-dioxaphospholane in 7 ml benzene. Stirring is continued for 2 h. The precipitate formed is removed by filtration and solvents are evaporated in vacuo to give 2.2 g of solid material, crude compound (V), to which 36 ml acetonitrile are added. The mixture is cooled to −15° C. Then 3.34 g (ca. 5 ml) trimethylamine are added, the reaction flask (500 ml round bottom flask) is sealed with a glass stopper fastened with wire. The mixture is stirred at 60° C. for 24 h. Evaporation of solvents in vacuo gives 2.2 g of crude 1-(1-imidazolyl)-2-deoxy-2-O-octadecyl-glycero-3-phosphocholine which is purified by column chromatography on silica gel. column 15×1.5 cm; solvents:

1. chloroform-methanol-2N ammonia (85:15:2; 306 ml); and
2. chloroform-methanol-ammonia (80:20:4; 208 ml).

Flow rate 12 ml/min. Fraction (12 ml) are collected and monitored by TLC, using chloroform-methanol-25% ammonia (40:30:6) as the developing solvent. Rf of the product is 0.19. Fractions 17–32 (solvent 2) are combined and give, after evaporation of the solvent, 0.78 g of pure product (50% yield) as a white solid. Identity of the product, 1-(1-imidazolyl)-2-deoxy-2-O-octadecyl-glycero-3-phosphocholine, is confirmed by $^{13}C$ and $^1H$ NMR.

EXAMPLE 32

A. Injection- For 1000 Ampules:

| Ingredients | Amount |
| --- | --- |
| Active Compound | 5 g |
| Buffering Agents | q.s. |
| Propylene glycol | 400 mg |
| Water for injection | 600 mL |

The active compound and buffering agents are dissolved in the propylene glycol at about 50° C. The water for injection is then added with stirring and the resulting solution is filtered, filled into ampules, sealed and sterilized by autoclaving.

B. Capsule- For 1000 Capsules:

| Ingredients | Amount |
| --- | --- |
| Active Compound | 50 g |
| Lactose | 450 g |
| Magnesium stearate | 5 g |

The ingredients are thoroughly mixed and packed into gelatin capsules.

C. Ointment

| Ingredients | Amount |
| --- | --- |
| Active Compound | 0.1–5% |
| Ointment base (white petrolatum and mineral oil) | q.s. |

An ointment base consisting of mineral oil and white petrolatum is prepared using relative proportions of each to achieve the desired viscosity. The active compound is added and thoroughly blended to form a homogeneous ointment. For treating psoriasis, an effective amount of a topical corticosteroid, such as 0.05% betamethasone dipropionate or 0.1% triamcinolone acetonide, may also be blended into the ointment.

D. Tablets- For 1000 Tablets:

| Ingredients | Amount |
| --- | --- |
| Active Compound | 50 g |
| Starch | 20 g |
| Magnesium stearate | 1 g |

The active compound and the starch are granulated with water and dried. The magnesium stearate is added to the dried granules and the mixture is thoroughly blended and molded into tablets.

While the invention has been described herein with some specificity, those of skill will recognize variations and modifications of what has been described that are within the spirit of the invention. It is intended that the invention also entails such variations and modifications.

What is claimed is:

1. Heteroaryl substituted glycero-phosphoethanolamines of formulas Ia, Ib and Ic:

$$\begin{array}{l} CH_2-O-R \\ | \\ CH-Het \\ | \\ CH_2-O-PEA \end{array} \quad \text{Ia}$$

$$\begin{array}{l} CH_2-O-R \\ | \\ CH-O-PEA \\ | \\ CH_2-Het \end{array} \quad \text{Ib}$$

$$\begin{array}{l} CH_2-O-PEA \\ | \\ CH-O-R \\ | \\ CH_2-Het \end{array} \quad \text{Ic}$$

and enantiomeric and cis- and trans-geometric isomers thereof, wherein R represents a substituted or unsubstituted straight or branched chain $C_{10-24}$ alkyl or alkenyl, said substituent being one or more of halo, $C_{1-3}$ alkoxy or cyano, provided that a double bond of said alkenyl does not involve the carbon atom of said alkenyl that is bonded to the oxygen atom of the glyceryl chain; Het represents a 5- to 9-membered heteroaryl mono- or bicyclic ring system with 1 to 4 nitrogen atoms as the sole hetero atoms, one of which nitrogen atoms is bonded to the carbon atom of the glyceryl chain; and PEA, together with the oxygen atom of the glyceryl chain to which PEA is bonded, represents a phosphoethanolamine of the formula:

$$-O-\overset{\overset{O}{\|}}{\underset{\underset{O^-}{|}}{P}}-O-(CH_2)_2-\overset{\overset{R^1}{|}}{\underset{\underset{R^3}{|}}{N^+}}-R^2$$

wherein $R^1$, $R^2$ and $R^3$ are each hydrogen or methyl, provided that at least one of $R^1$, $R^2$ and $R^3$ is methyl; and the pharmaceutically acceptable salts thereof.

2. A glycerophosphoethanolamine of claim 1 wherein Het is imidazolyl or 1-triazolyl.

3. A glycerophosphoethanolamine of claim 1 which is of Formula Ia.

4. A glycerophosphoethanolamine of claim 1 which is of Formula Ia wherein Het is imidazolyl or 1-triazolyl.

5. A glycerophosphoethanolamine of claim 1 wherein said R is $C_{14-20}$ alkyl or $C_{14-20}$ alkenyl.

6. A glycerophosphoethanolamine of claim 1 wherein said R is $C_{16-18}$ alkyl or $C_{16-18}$ alkenyl.

7. A glycerophosphoethanolamine of claim 1 wherein $R^1$, $R^2$, and $R^3$ are methyl.

8. A glycerophosphoethanolamine of claim 1 which is of Formula Ia wherein Het is imidazolyl or 1-triazolyl, R is $C_{16-18}$ alkyl, and $R^1$, $R^2$, and $R^3$ are methyl.

9. A compound of claim 1 which is selected from the group consisting of:

1-O-octadecyl-2-(1-imidazolyl)-2-deoxy-glycero-3-phosphocholine;

1-O-octadecyl-2-(1-triazolyl)-2-deoxy-glycero-3-phosphocholine; and

1-O-hexadecyl-2-(1-imidazolyl)-2-deoxy-glycero-3-phosphocholine.

10. A method of treating a tumor in a mammal comprising administering to said mammal an anti-tumor-effective amount of a glycero-phosphoethanolamine of Formula Ia, Ib, or Ic:

$$\begin{array}{l} CH_2-O-R \\ | \\ CH-Het \\ | \\ CH_2-O-PEA \end{array} \quad \text{Ia}$$

$$\begin{array}{l} CH_2-O-R \\ | \\ CH-O-PEA \\ | \\ CH_2-Het \end{array} \quad \text{Ib}$$

$$\begin{array}{l} CH_2-O-PEA \\ | \\ CH-O-R \\ | \\ CH_2-Het \end{array} \quad \text{Ic}$$

or any of the enantiomeric and cis- and trans-geometric isomers thereof, wherein R represents a substituted or unsubstituted straight or branched chain $C_{10-24}$ alkyl or alkenyl, said substituent being one or more of halo, $C_{1-3}$ alkoxy or cyano, provided that a double bond of said alkenyl does not involve the carbon atom of said alkenyl that is bonded to the oxygen atom of the glyceryl chain; Het represents a 5- to 9-membered heteroaryl mono- or bicyclic ring system with 1 to 4 nitrogen atoms as the sole hetero atoms, one of which nitrogen atoms is bonded to the carbon atom of the glyceryl chain; and PEA, together with the oxygen atom of the glyceryl chain to which PEA is bonded, represents a phosphoethanolamine of the formula:

$$-O-\overset{\overset{O}{\|}}{\underset{\underset{O^-}{|}}{P}}-O-(CH_2)_2-\overset{\overset{R^1}{|}}{\underset{\underset{R^3}{|}}{N^+}}-R^2$$

wherein $R^1$, $R^2$ and $R^3$ are each hydrogen or methyl, provided that at least one of $R^1$, $R^2$ and $R^3$ is methyl; or a pharmaceutically acceptable salt thereof.

11. The method of claim 10 wherein said glycerophosphoethanolamine is a compound of Formula Ia.

12. The method of claim 10 wherein said glycerophosphoethanolamine is a compound of Formula Ia in which Het is imidazolyl or 1-triazolyl, R is $C_{16-18}$ alkyl and $R^1$, $R^2$ and $R^3$ are methyl.

13. The method of claim 10 wherein said glycerophosphoethanolamine is selected from the group consisting of:

1-O-octadecyl-2-(1-imidazolyl)-2-deoxy-glycero-3-phosphocholine;

1-O-octadecyl-2-(1-triazolyl)-2-deoxy-glycero-3-phosphocholine; and

1-O-hexadecyl-2-(1-imidazolyl)-2-deoxy-glycero-3-phosphocholine.

14. A method of treating psoriasis in a mammal comprising administering to said mammal an anti-psoriatic-effective amount of a glycerophosphoethanolamine of Formula Ia, Ib or Ic:

$$\begin{array}{l} CH_2-O-R \\ | \\ CH-Het \\ | \\ CH_2-O-PEA \end{array} \quad \text{Ia}$$

$$\begin{array}{l} CH_2-O-R \\ | \\ CH-O-PEA \\ | \\ CH_2-Het \end{array} \quad \text{Ib}$$

-continued

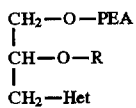   Ic or any of the enantiomeric and cis- and trans-geometric isomers thereof, wherein R represents a substituted or unsubstituted straight or branched chain $C_{10-24}$ alkyl or alkenyl, said substituent being one or more of halo, $C_{1-3}$ alkoxy or cyano, provided that a double of said alkenyl does not involve the carbon atom of said alkenyl that is bonded to the oxygen atom of the glyceryl chain; Het represents a 5- to 9-membered heteroaryl mono- or bicyclic ring system with 1 to 4 nitrogen atoms as the sole hetero atoms, one of which nitrogen atoms is bonded to the carbon atom of the glyceryl chain; and PEA, together with the oxygen atom of the glyceryl chain to which PEA is bonded, represents a phosphoethanolamine of the formula:

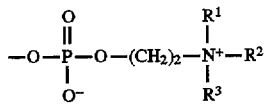

wherein $R^1$, $R^2$ and $R^3$ are each hydrogen or methyl, provided that at least 1 of $R^1$, $R^2$ and $R^3$ is methyl; or a pharmaceutically acceptable salt thereof.

15. The method of claim 14 wherein said glycero-phosphoethanolamine is a compound of Formula Ia.

16. The method of claim 14 wherein said glycero-phosphoethanolamine is a compound of Formula Ia in which Het is imidazolyl or 1-triazolyl, R is $C_{16-18}$ alkyl, and $R^1$, $R^2$ and $R^3$ are methyl.

17. The method of claim 14 wherein said glycero-phosphoethanolamine is selected from the group consisting of:
- 1-O-octadecyl-2-(1-imidazolyl)-2-deoxy-glycero-3-phosphocholine;
- 1-O-octadecyl-2-(1-triazolyl)-2-deoxy-glycero-3-phosphocholine; and
- 1-O-hexadecyl-2-(1-imidazolyl)-2-deoxy-glycero-3-phosphocholine.

18. A method of treating inflammation in a mammal comprising administering to said mammal an anti-inflammatory-effective amount of a glycerophosphoethanolamine of Formula Ia, Ib or Ic:

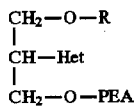   Ia

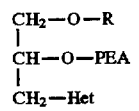   Ib

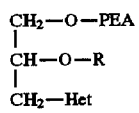   Ic or any of the enantiomeric and cis- and trans-geometric isomers thereof, wherein R represents a substituted or unsubstituted straight or branched chain $C_{10-24}$ alkyl or alkenyl, said substituent being one or more of halo, $C_{1-3}$ alkoxy or cyano, provided that a double bond of said alkenyl does not involve the carbon atom of said alkenyl that is bonded to the oxygen atom of the glyceryl chain; Het represents a 5- to 9-membered heteroaryl mono- or bicyclic ring system with 1 to 4 nitrogen atoms as the sole hetero atoms, one of which nitrogen atoms is bonded to the carbon atom of the glycero chain; and PEA, together with the oxygen atom of the glyceryl chain to which PEA is bonded, represents a phosphoethanolamine of the formula:

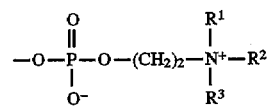

wherein $R^1$, $R^2$ and $R^3$ are each hydrogen or methyl, provided that at least one of $R^1$, $R^2$ and $R^3$ is methyl; or a pharmaceutically acceptable salt thereof.

19. The method of claim 18 wherein said glycero-phosphoethanolamine is a compound of Formula Ia.

20. The method of claim 18 wherein said glycero-phosphoethanolamine is a compound of Formula Ia in which Het is imidazolyl or 1-triazolyl, R is $C_{16-18}$ alkyl, and $R^1$, $R^2$ and $R^3$ are methyl.

21. The method of claim 18 wherein said glycero-phosphoethanolamine is selected from the group consisting of:
- 1-O-octadecyl-2-(1-imidazolyl)-2-deoxy-glycero-3-phosphocholine;
- 1-O-octadecyl-2-(1-triazolyl)-2-deoxy-glycero-3-phosphocholine; and
- 1-O-hexadecyl-2-(1-imidazolyl)-2-deoxy-glycero-3-phosphocholine.

22. A pharmaceutical composition comprising an anti-tumor, anti-psoriatic or anti-inflammation-effective amount of a heteroaryl substituted glycero-phosphoethanolamine of Formulas Ia, Ib or Ic:

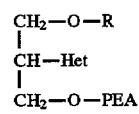   Ia

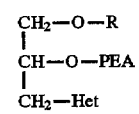   Ib

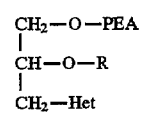   Ic or any of the enantiomeric cis- and trans-geometric isomers thereof, wherein R represents a substituted or unsubstituted straight or branched chain $C_{10-24}$ alkyl or alkenyl, said substituent being one or more of halo, $C_{1-3}$ alkoxy or cyano, provided that a double bond of said alkenyl does not involve the carbon atom of said alkenyl that is bonded to the oxygen atom of the glyceryl chain; Het represents a 5- to 9-membered heteroaryl mono- or bicyclic ring system with 1 to 4 nitrogen atoms as the sole hetero atoms, one of which nitrogen atoms is bonded to the carbon atom of the glyceryl chain; and PEA, together with the oxygen atom of the glyceryl chain to which PEA is bonded, represents a phosphoethanolamine of the formula:

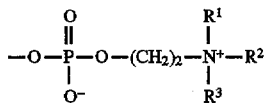

wherein $R^1$, $R^2$ and $R^3$ are each hydrogen or methyl, provided that at least one of $R^1$, $R^2$ and $R^3$ is methyl; or a pharmaceutically acceptable salt thereof.

23. The composition of claim 22 wherein Het is imidazolyl or 1-triazolyl.

24. The composition of claim 22 wherein said glycerophosphoethanolamine is a compound of Formula Ia.

25. The composition of claim 22 wherein R is selected from the group consisting of $C_{14-20}$ alkyl and $C_{14-20}$ alkenyl.

26. The composition of claim 22 wherein R is selected from the group consisting of $C_{16-18}$ alkyl and $C_{16-18}$ alkenyl.

27. The composition of claim 22 wherein said glycerophosphoethanolamine is a compound of Formula Ia wherein Het is imidazolyl or 1-triazolyl, R is $C_{16-18}$ alkyl, and $R^1$, $R^2$ and $R^3$ are methyl.

28. The composition of claim 22 wherein said glycerophosphoethanolamine is selected from the group consisting of:

1-O-octadecyl-2-(1-imidazolyl)-2-deoxy-glycero-3-phosphocholine;

1-O-octadecyl-2-(1-triazolyl)-2-deoxy-glycero-3-phosphocholine; and

1-O-hexadecyl-2-(1-imidazolyl)-2-deoxy-glycero-3-phosphocholine.

29. A pharmaceutical composition for topical use comprising from about 0.1 to about 5.0 weight percent of a compound of claim 1 and a pharmaceutically acceptable carrier in ointment form.

30. The topical composition of claim 29 wherein said compound is a compound of Formula Ia wherein Het is imidazolyl or 1-triazolyl, R is $C_{16-18}$ alkyl, and $R^1$, $R^2$ and $R^3$ are methyl.

31. The topical composition of claim 29 wherein said compound is selected from the group consisting of:

1-O-octadecyl-2-(1-imidazolyl)-2-deoxy-glycero-3-phosphocholine;

1-O-octadecyl-2-(1-triazolyl)-2-deoxy-glycero-3-phosphocholine; and

1-O-hexadecyl-2-(1-imidazolyl)-2-deoxy-glycero-3-phosphocholine.

* * * * *